United States Patent [19]

Sohn et al.

[11] Patent Number: 4,891,057
[45] Date of Patent: Jan. 2, 1990

[54] PHENYLPYRAZOLECARBOXYLIC ACID DERIVATIVES, THEIR PREPARATION, AND THEIR USE AS PLANT-GROWTH REGULATORS AND SAFENERS

[75] Inventors: Erich Sohn, Esslingen; Reinhard Handte, Gablingen; Hilmar Mildenberger, Kelkheim; Helmut Bürstell, Frankfurt am Main; Klaus Bauer, Hanau; Hermann Bieringer, Eppstein, all of Fed. Rep. of Germany

[73] Assignee: Hoechst Aktiengesellschaft, Frankfurt am Main, Fed. Rep. of Germany

[21] Appl. No.: 104,820

[22] Filed: Oct. 2, 1987

[30] Foreign Application Priority Data

Oct. 4, 1986 [DE] Fed. Rep. of Germany ....... 3633840

[51] Int. Cl.$^4$ .................. A01N 43/56; C07D 231/14
[52] U.S. Cl. .......................................... 71/72; 71/74; 71/76; 71/92; 548/377; 548/378
[58] Field of Search ............... 548/377, 378, 143, 146, 548/152, 178, 179, 217, 238, 254, 255, 269, 327, 336, 374; 71/92, 90, 72, 74, 76; 544/55, 66, 96, 140, 333; 546/211, 279

[56] References Cited

U.S. PATENT DOCUMENTS 4,563,210  1/1986  Beck et al. .......................... 548/377
4,620,865 11/1986  Beck et al. .......................... 548/377

*Primary Examiner*—Robert W. Ramsuer
*Attorney, Agent, or Firm*—Curtis, Morris & Safford

[57] ABSTRACT

Compounds of the formula I

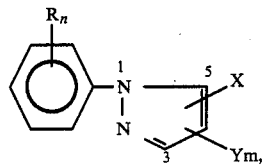

in which R denotes halogen, hydroxyl, cyano, nitro, (substituted) alkyl, (substituted) alkoxy, (halo)alkylthio, carboxyl, alkoxycarbonyl; (halo)alkylsulf(inyl)(onyl) or —(onyloxy); (halo)phenyl or (halo)phenoxy; X in the 3- or 5-position denotes a (thio)carboxylic acid—or an optionally heterocyclic radical which is derived therefrom; Y denotes halogen, m denotes the number 0 or 1, and n denotes a number from 0 to 5, have valuable plant growth-regulating properties and are suitable, in addition, as safeners for protecting crop plants against phytotoxic side effects of herbicides.

14 Claims, No Drawings

PHENYLPYRAZOLECARBOXYLIC ACID DERIVATIVES, THEIR PREPARATION, AND THEIR USE AS PLANT-GROWTH REGULATORS AND SAFENERS

DESCRIPTION

Phenylpyrazolecarboxylic acid derivatives, their preparation, and their use as plant-growth regulators and safeners.

Phenylaminopyrazoles having a herbicidal action have been disclosed, for example by EP-A 138,149.

Novel phenylpyrazolecarboxylic acid derivatives have been found which have surprisingly excellent plant growth-regulating properties and, in addition, reduce phytotoxic side effects of herbicides on crop plants.

The present invention therefore relates to compounds of the formula I

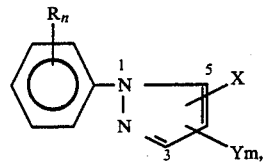

in which

R, in each case independently of one another, denote halogen, hydroxyl, cyano, nitro, $(C_1-C_4)$alkyl, halo$(C_1-C_4)$alkyl, $(C_1-C_4)$alkoxy$(C_1-C_4)$alkyl, $(C_1-C_6)$alkoxy, $(C_1-C_6)$alkoxy$(C_1-C_4)$alkoxy, halo$(C_1-C_6)$alkoxy, $(C_1-C_4)$alkylthio, halo$(C_1-C_4)$alkylthio, carboxyl, $(C_1-C_4)$alkoxycarbonyl, $(C_1-C_4)$alkylsulfinyl, halo$(C_1-C_4)$alkylsulfinyl, $(C_1-C_4)$alkylsulfonyl, halo$(C_1-C_4)$alkylsulfonyl, $(C_1-C_4)$alkylsulfonyloxy, halo$(C_1-C_4)$alkylsulfonyloxy, phenyl, halophenyl, phenoxy or halophenoxy, X is oriented in the 3- or 5-position of the pyrazole ring and denotes as radical of the formula

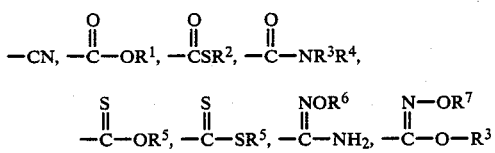

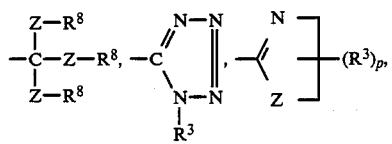

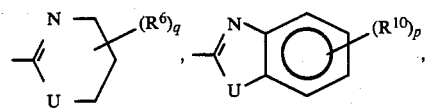

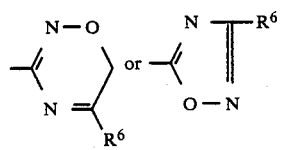

Y denotes halogen,

Z denotes O or S,

U denotes O, S or N-$R^6$, $R^1$ denotes hydrogen, $(C_1-C_{12})$alkyl, $(C_1-C_{12})$alkyl which is monosubstituted or polysubstituted by halogen and/or monosubstituted or disubstituted by hydroxyl, $(C_1-C_6)$alkoxy, $(C_1-C_4)$alkoxy-$(C_1-C_4)$alkoxy, $(C_1-C_4)$alkylthio, $(C_1-C_4)$alkylsulfinyl, $(C_1-C_4)$alkylsulfonyl, mono- or di-$(C_1-C_4$-alkyl)amino, cyano, aminocarbonyl, $(C_1-C_4)$alkylcarbonyl, $(C_1-C_4$-alkoxy)carbonyl, cyclo$(C_3-C_7)$alkyl, tri$(C_1-C_4)$alkylsilyl, benzyloxy, benzyloxyethoxy, phenyl, phenyl which is substituted by halogen or $(C_1-C_4)$alkyl, phenoxy or phenylthio which both are unsubstituted or substituted by halogen or $(C_1-C_4)$alkyl; by oxiranyl, tetrahydrofuryl, triazolyl, pyridinyl, imidazolyl, carboxyl, carboxylate with a cation which can be employed for agriculture, or the —O—N=$C(CH_3)_2$ radical; or denotes $(C_3-C_6)$-alkenyl, halo$(C_3-C_6)$alkenyl, CYC10$(C_3-C_7)$alkyl which is unsubstituted or substituted by halogen or $(C_1-C_4)$-alkyl; cyclo$(C_5-C_7)$alkenyl which is unsubstituted or substituted by halogen or $(C_1-C_4)$alkyl; or denotes $(C_3-C_6)$-alkynyl, 1,2-epoxyprop-3-yl, phenyl or phenyl which is monosubstituted by halogen, nitro, cyano, $(C_1-C_4)$alkyl, $(C_1-C_4$-alkoxy)carbonyl or $(C_1-C_4)$alkoxy; or denotes $(C_1-C_4$-alkyl)carbonyl, phenylcarbonyl with a phenyl ring which is unsubstituted or substituted by halogen, nitro, cyano or $(C_1-C_4)$alkyl; or denotes a radical of the formula $-N=C(R^{10})_2$, $-NR^3R^{11}$,

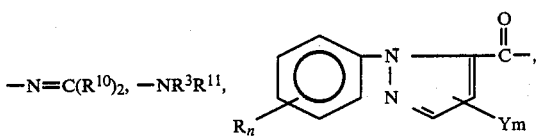

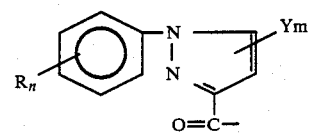

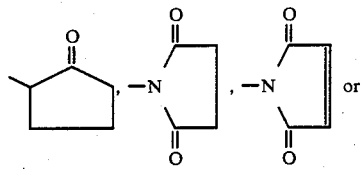

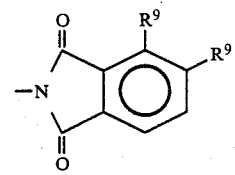

or a cation which can be employed for agriculture, $R^2$ denotes $(C_1-C_{12})$alkyl or $(C_1-C_{12})$alkyl which is monosubstituted or disubstituted by $(C_1-C_4)$alkoxyethoxy, cyclo$(C_3-C_6)$alkyl, benzyloxy, phenyl, phenoxy, $(C_1-C_4)$alkylthio, $(C_1-C_4$-alkoxy)carbonyl, carboxyl or carboxylate with a cation which can be employed for agriculture, $R^3$, in each case independently of one another, denote $(C_1-C_6)$alkyl, phenyl or $(C_3-C_6)$alkenyl, $R^4$ denotes hydrogen, $(C_1-C_{12})$alkyl or $(C_1-C_{12})$alkyl which is monosubstituted or disubstituted by $(C_1-C_6)$- alkoxy, $(C_1-C_4)$alkoxyethoxy, hydroxyl, hydroxyimino, $(C_1-C_4)$alkoxyimino, halogen, cyclo$(C_3-C_6)$alkyl, benzyloxy, cyano, aminocarbonyl, carboxyl, $(C_1-C_4$-alkoxy)carbonyl, formyl, phenyl or phenoxy, or denotes phenyl or phenyl which is monosubstituted or disubstituted by halogen, nitro, cyano, $(C_1-C_4)$alkyl or $(C_1-C_4)$alkoxy; or denotes $(C_3-C_6)$alkenyl, $(C_3-C_6)$cycloalkyl, or a radical of the formula

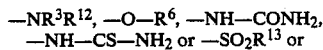

$R^3$ and $R^4$, together with the nitrogen atom to which they are bound, denote a saturated or unsaturated, three- to seven- membered ring which can be benzofused and which contains up to three heteroatoms from the group comprising O, N or S and is unsubstituted or substituted by $(C_1-C_4)$alkyl or halogen and can contain a carbonyl group, $R^5$ denotes H, $(C_1-C_6)$alkyl or phenyl, or in the case where X=—CS—$OR^5$, denotes a cation which can be employed for agriculture, $R^6$, in each case independently of one another, denote H, $(C_1-C_4)$alkyl or benzyl, $R^7$, in each case independently of one another, denote h,$(C_1-C_{12})$alkyl which is unsubstituted or substituted by phenyl which is unsubstituted or substituted by halogen, nitro, cyano, $(C_1-C_4)$alkyl or $(C_1-C_4)$alkoxy, by hydroxyl, cyano, $(C_1-C_4$-alkoxy)carbonyl, $(C_1-C_4)$alkylthio, $(C_1-C_4)$alkoxy, cyclo$(C_5-C_7)$alkyl or benzyloxy, or denote $(C_3-C_6)$alkenyl, halo$(C_3-C_6)$alkenyl, $(C_3-C_6)$alkynyl, cyclo$(C_5-C_8)$alkyl, cyclo$(C_5-C_6)$alkenyl, $(C_1-C_6$-alkyl)carbonyl, halo$(C_1-C_6$-alkyl)carbonyl, [$(C_1-C_6$-alkyl)amino]carbonyl, benzoyl, halobenzoyl or methylbenzoyl, $R^8$, in each case independently of one another, denote $(C_1-C_6)$alkyl which is unsubstituted or substituted by phenyl, cyclo$(C_5-C_7)$alkyl, $(C_1-C_4)$alkoxy, $(C_1-C_4)$alkylthio or halogen, or two radicals $R^8$, together with Z and the carbon atom to which they are bound, denote a 5- or 6-membered saturated heterocyclic ring which is unsubstituted or substituted by $(C_1-C_4)$-alkyl, hydroxy$(C_1-C_4)$alkyl, halo$(C_1-C_4)$alkyl or phenyl;

$R^9$, in each case independently of one another, denote H, halogen, $(C_1-C_4)$alkyl, nitro or cyano, $R^{10}$, in each case independently of one another, denote H, $(C_1-C_6)$alkyl which is unsubstituted or substituted by $(C_1-C_4)$alkoxy, triazolyl or imidazolyl; or denote cyclo$(C_3-C_6)$alkyl, $(C_3-C_6)$alkenyl, phenyl or benzyl, or in the radical —N=C$(R^{10})_2$ both radicals $R^{10}$, together with the carbon atom to which they are bound, denote a cyclo$(C_5-C_7)$alkyl which is unsubstituted or substituted by methyl or halogen, $R^{11}$ denotes $(C_1-C_4)$alkyl, phenyl, $(C_1-C_6$-alkyl)carbonyl, benzyl, benzoyl, halobenzoyl, halobenzoyl or methylbenzoyl, $R^{12}$ denotes H, $(C_1-C_4)$alkyl, formyl, $(C_1-C_6$-alkyl)carbonyl, benzoyl, halobenzoyl, methylbenzoyl or trihaloacetyl, $R^{13}$ denotes $(C_1-C_4)$alkyl, phenyl, or methylphenyl, m denotes 0 or 1, n denotes an integer from 0 to 5, in particular from 1 to 3, p denotes an integer from 0 to 4, in particular from 0 to 2, and q denotes an integer from 0 to 6, in particular from 0 to 3, and the salts and quaternization products thereof which are acceptable for agricultural purposes.

The salt formation or quaternization here occurs on the basic nitrogen atom of the pyrazole ring. Salt formation or quaternization is not possible when $R^1$ or $R^5$ denotes a cation or R, $R^1$ or $R^2$ contains a carboxylate group.

Preferred compounds of the formula I are, in particular, those in which R denotes halogen, $(C_1-C_4)$alkyl, halo$(C_1-C_4)$alkyl or $(C_1-C_4)$alkoxy; X denotes CN, —$COOR^1$, CO—$SR^2$ or —$CONR^3R^4$; Y denotes halogen; $R^1$ and $R^2$ denotes H, $(C_1-C_4)$alkyl, $(C_2-C_4)$alkenyl, $(C_2-C_4)$alkynyl, $(C_1-C_4)$alkoxy-$(C_1-C_4)$alkyl or a cation; $R^3$ and $R^4$ denote H or $(C_1-C_4)$alkyl, m denotes 0 or 1, and n denotes 1 to 3. Compounds where $R_n$=2,6-dialkyl, mono- or di-halo or mono-trifluoromethyl are of particular interest here.

The radical Y is oriented, in particular, in the 4-position of the pyrazole ring.

Halogen is taken to mean F, Cl, Br or I, in particular F, Cl or Br.

Halo$(C_1-C_4)$alkyl contains 1 to 5, in particular 1 to 3, chlorine or fluorine atoms; the $CF_3$ radical is preferred.

Halogenated $(C_1-C_{12})$alkyl contains, in particular, 1 to 13 chlorine or fluorine atoms; this includes, for example, the 2,2,2-trichloroethyl, 4-chlorobutyl, 2,2,2-trifluoroethyl, 1,1,1,3,3,3-hexafluoroprop-2-yl, 2,2,3,4,4,4-hexafluorobutyl and 3,3,4,4,5,5,6,6,7,7,8,8,8-tridecafluorooct-1-yl radicals.

Halo$(C_1-C_6)$alkylthio, halo$(C_1-C_4)$alkylsulfinyl, halo$(C_1-C_4)$alkylsulfonyl and halo$(C_1-C_4)$alkylsulfonyloxy in each case contain, in particular, 1 to 9 chlorine or fluorine atoms; halogenated $(C_3-C_6)$alkenyl contains, in particular, 1 to 3 chlorine or fluorine atoms.

Halophenyl, halobenzyl and halobenzoyl contain, in particular, 1 to 3 fluorine, chlorine or bromine atoms.

Trihaloacetyl is taken to mean, in particular, trichloroacetyl and trifluoroacetyl.

In the case where the —$NR^3R^4$ radical (for X=CO—$NR^3R^4$) forms a heterocyclic ring, this is taken to mean, for example, piperidine, morpholine, 2,6-dimethylmorpholine, piperazine, triazole, imidazole, pyrazole, thiazole and benzimidazole.

In the case where, in the substituents listed—in addition to the pyrazole ring—further basic nitrogen atoms occur, multiple salt formation or quaternization is also possible.

All inorganic or organic acids which are capable, as a consequence of their pKs value, of salt formation, for example hydrohalic acids, nitric acid, sulfuric acid, phosphoric acid, phosphonic acids, sulfonic acids, haloacetic acids or oxalic acid, are suitable for preparing the salts.

Quaternization products are taken to mean the products of the reaction of alkyl, alkylthioalkyl, alkoxyalkyl, in particular $(C_1-C_6)$alkyl and phenylacyl, optionally substituted, in particular halogenated, in the phenyl radical, halides. The quaternization products of the compounds of the formula I are prepared by generally conventional methods.

Possible cations for $R^1$, $R^2$ or $R^5$ which can be employed in agriculture are metallic cations, for example alkali metal or alkaline-earth metal cations, such as Na, K or Mg, or organic cations, such as organically substituted ammonium, organically substituted phosphonium, sulfonium or sulfoxonium, or other nitrogen cations.

Organically substituted ammonium denotes primary, secondary, tertiary or quaternary, aliphatic, aromatic or heteroaromatic ammonium which may contain 1 to three nitrogen atoms. The nitrogen atoms of the amine can in this case also be part of a cyclic system. Examples of such ammonium salts which may be mentioned are: mono-, di-, tri- or tetra[($C_1$-$C_6$)alkyl]ammonium, such as isopropylammonium, butylammonium, stearylammonium or triethylammonium, mono-, di- or tri[($C_1$-$C_4$)alkoxy($C_1$-$C_4$)alkyl]ammonium or mono-, di-, or tri[($C_1$-$C_6$)alkanol]ammonium, such as methoxyethylammonium, methoxypropylammonium, triethanolammonium or tripropanolammonium, or ammonium compounds containing mixed radicals, such as tert.-butyldiethanolammonium, triethylbenzylammonium, hydroxyethyltrimethylammonium or chloroethyltrimethylammonium, or allylammonium, diallylammonium, cyclohexylammonium, menthanylammonium, aminoethylammonium, ethylendiammonium, benzohydrylammonium, pyrrolidinium, morphilinium, 3-pyridylammonium, piperidinium or piperazinium, or an ammonium which is derived from an amino acid or its ester, such as [$NH_3$—$CH_2$—$COOCH_3$]⁺.

Organically substituted phosphonium, organic sulfonium or organic sulfoxonium contain aliphatic or arylaliphatic radicals as specified for ammonium.

Other nitrogen cations are, for example, hydrazonium, hydroxylammonium, guanidinium and aminoguanidinium, or the substitution products thereof.

The invention furthermore relates to a process for the preparation of the compounds of the formula I, wherein a compound of the formula II

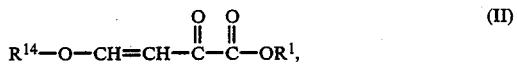

in which $R^{14}$ denotes ($C_1$-$C_6$)alkyl, is reacted with a compound of the formula III

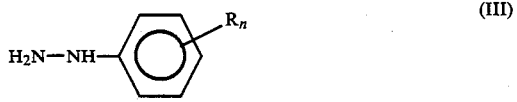

and is subsequently derivatized, if appropriate.

The process is carried out at 0° to 120° C. in an organic solvent, if appropriate in the presence of an organic acid, such as p-toluenesulfonic acid or methanesulfonic acid. Solvents which can be employed are polar compounds, such as alcohols, for example ethanol or methanol, organic acids, such as glacial acetic acid, chlorinated hydrocarbons, such as dichloroethane, or aromatic solvents, such as toluene or xylene.

During the reaction, compounds of the formulae IVa and IVb

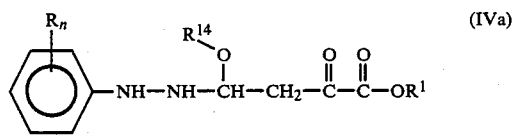

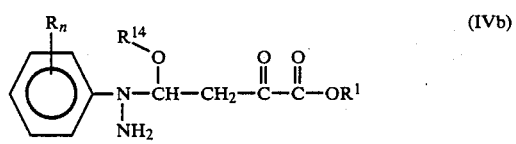

are produced as intermediates. These intermediates can be isolated and subsequently cyclized under the conditions described above. In the direct further reaction, mixtures of the compounds of the formula I, i.e. the compounds of the formulae Ia and Ib, are generally obtained alongside one another.

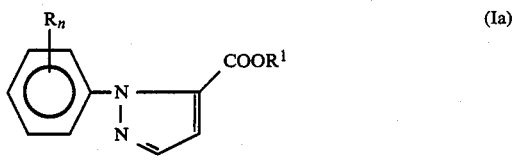

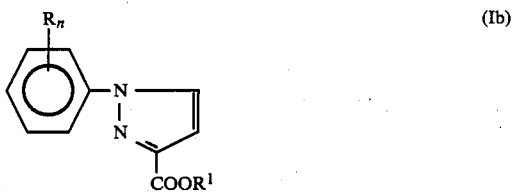

The compounds of the formulae (Ia) and (Ib) can be derivatized by conventional processes at the —$COOR^1$ group or by halogenating the pyrazole radical.

Thus, the pyrazoles of the formulae Ia and Ib can be halogenated at the 4-position of the pyrazole radical under conventional aromatic halogenation conditions, see Houben-Weyl, Methoden der organischen Chemie [Methods of Organic Chemistry], volume 5/3, pp. 503 ff, volume 5/4, pp. 13 ff (1962). For derivatization, the —$COOR^1$ radical is furthermore converted in a known fashion into other radicals mentioned for X, for example by saponification, esterification, transesterification, amidation, salt-formation etc., as described, for example, in German Offenlegungsschriften 3,44,918 and 3,442,690, or salt-formation or quaternization takes place in a conventional fashion on the basic nitrogen atom of the pyrazole ring.

The starting compounds of the formula II can be obtained by reaction of the compounds of the formula V with compounds of the formula VI

in the presence of an organic auxiliary base (literature: Chem. Ber. 115, pp. 2466-2782 (1982)). $R^{15}$ denotes a leaving group, such as Cl, Br or $OSO_2CF_3$.

Auxiliary bases which can be employed are organic amines, such as triethylamine or pyridine. The process can be carried out between −20° and +30° C. The compounds of the formula II obtained can be further reacted directly without work-up. The starting compounds of the formula III can be prepared by conventional processes, see Houben-Weyl, Methoden der organischen Chemie [Methods of Organic Chemistry], vol. 10/2, p. 169 (1967).

The invention furthermore relates to the use of the compounds of the formula I as plant-growth regulators. Typical growth-regulating effects can be achieved using the compounds according to the invention. The compounds have a regulating effect on the plant's inherent metabolism and can thus be employed for influencing plant substances in a specific fashion and for simplifying harvesting, such as for initiating desiccation and inhibiting growth. In addition, they are suitable for general control and inhibition of undesired vegetative growth without at the same time killing the plants. Inhibition of vegetative growth plays an important part in many monocotyledon and dicotyledon crops since lodging can thereby be reduced or completely prevented. The growth-regulating activity of the compounds as growth inhibitors in cereals, corn, soybean, tobacco, cotton, field beans, rape, rice, sunflowers and grass, and their ability to increase the content of desired substances such as carbohydrates (for example sugar cane or millet crops) and protein in the case of crop plants should be particularly emphasized. Finally, the compounds exhibit a very great improvement in fruit abscission, in particular in citrus fruit.

A further solution of the object set are also plant growth-regulating agents which are distinguished by an active content of at least one of the compounds according to the invention. The application rate of the compounds of the formula I is generally 0.02 to 2.5 kg of active ingredient per ha, preferably 0.05 to 1.5 kg/ha. In practical use, the compounds according to the invention can also be advantageously combined, if desired, with known growth regulators or natural or vegetative hormones.

The invention furthermore relates to the use of the compounds of the formula I as safeners. Thus, it has been found that they reduce or completely prevent phytotoxic side effects of plant-protection agents, in particular herbicides, when used in crops of useful plants.

The compounds of the formula I can be applied together with other herbicides, and are then capable of antagonizing or completely neutralizing damaging side effects of these herbicides without impairing the herbicidal activity of these herbicides against weeds. This allows the area of application of conventional plant-protection agents to be very considerably widened. Such compounds, which have the property of protecting crop plants against phytotoxic damage by herbicides, are known as antidotes or "safeners".

Herbicides whose phytotoxic side effects can be reduced by means of the compounds of the formula I are, for example, carbamates, thiocarbamates, haloacetanilides, substituted phenoxy-, naphthoxy-and phenoxyphenoxycarboxylic acid derivatives and also heteroaryloxyphenoxycarboxylic acid derivatives, such as quinolyloxy-, quinoxalyloxy-, pyridyloxy-, benzoxazolyloxy- and benzothiazolyloxyphenoxycarboxylic acid esters, and furthermore dimedone oxime derivatives. Of these, phenoxyphenoxy- and heteroaryloxyphenoxycarboxylic acid esters are preferred. Suitable esters here are, in particular, lower alkyl, alkenyl and alkynyl esters.

The following herbicides may be mentioned as examples, without representing a limitation thereby:

(A) Herbicides of the ($C_1$–$C_4$)alkyl, ($C_2$–$C_4$)alkenyl and ($C_3$–$C_4$)alkynyl phenoxyphenoxy- and heteroaryloxyphenoxycarboxylates, such as
  methyl 2-(4-(2,4-dichlorophenoxy)-phenoxy)-propionate, methyl 2-(4-(4-bromo-2-chlorophenoxy)-phenoxy)propionate,
  methyl 2-(4-(4-trifluoromethylphenoxy)-phenoxy)-propionate,
  methyl 2-(4-(2-chloro-4-trifluoromethylphenoxy)-phenoxy)-propionate,
  methyl 2-(4-(2,4-dichlorobenzyl)-phenoxy)-propionate, ethyl 4-(4-(4-trifluoromethylphenoxy)-phenoxy)-pent-2-enoate,
  ethyl 2-(4-(3,5-dichloropyridyl-2-oxy)-phenoxy)propionate, propargyl 2-(4-(3,5-dichloropyridyl-2-oxy)-phenoxy)propionate,
  trimethylsilylmethyl 2-(4-(3,5-dichloropyridyl-2-oxy)phenoxy)-propionate,
  ethyl 2-(4-(6-chlorobenzoxazol-2-yloxy)-phenoxy)-propionate,
  ethyl 2-(4-(6-chlorobenzothiazol-2-yloxy)-phenoxy)-propionate.
  methyl 2-(4-(3-chloro-5-trifluoromethyl-2pyridyloxy)phenoxy)-propionate,
  ethyl 2-(4-(3-chloro-5-trifluoromethyl-2-pyridyloxy)-phenoxy)-propionate,
  butyl 2-(4-(5-trifluoromethyl-2-pyridyloxy)-phenoxy)propionate,
  ethyl 2-(4-(6-chloro-2-quinoxalyloxy)-phenoxy)propionate,
  ethyl 2-(4-(6-fluoro-2-quinoxalyloxy)-phenoxy)propionate, and
  ethyl 2-(4-(6-chloro-2-quinolyloxy)-phenoxy)propionate,
(B) chloroacetanilide herbicides, such as
  N-methoxymethyl-2,6-diethylchloroacetanilide,
  N-(3′-methoxyprop-2′-yl)-methyl-6-ethyl-chloroaacetanilide, and
  N-(3-methyl-1,2,4-oxadiazol-5-ylmethyl)-2,6-chloracetanilide,
(C) thiocarbamates, such as
  S-ethyl N,N-dipropylthiocarbamate or
  S-ethyl N,N-diisobutylthiocarbamate,
(D) dimedone derivatives, such as
  2-(N-ethoxybutyrimidoyl)-5-(2-ethylthiopropyl)-3-hydroxy-2-cyclohexen-1-one,
  2-(N-ethoxybutyrimidoyl)-5-(2-phenylthiopropyl)-3-hydroxy-2-cyclohexen-1-one,
  2(1-allyloxyiminobutyl)-4-methoxycarbonyl-5, 5′-dimethyl-3-oxocyclohexenol,
  2-(N-ethoxypropionamidoyl)-5-mesityl-3-hydroxy-2-cyclohexen-1one, and
  2(N-ethoxybutrimidoyl)-3-hydroxy-5-(thian-3-yl)-2-cyclohexen-1-one.

The safener:herbicide amount ratio can vary within broad limits, in the range between 1:10 and 10:1, in particular between 2:1 and 1:10. The ideal amounts of each of herbicide and safener depend on the type of herbicide or safener used and on the species of the plant crop to be treated, and can be determined from case to case by appropriate trials.

The major areas of application for the use of safeners are, above all, cereal crops (wheat, rye, barley and oats), rice, corn, sorghum, but also cotton, sugar beet, sugar cane and soybean.

Depending on their properties, the safeners of the formula I can be used for pretreatment of the seed of the crop plant (seed dressing), introduced into the seed drills before sowing, or applied together with the herbicide before or after emergence of the plant. Pre-emergence treatment includes treatment of the cultivated area before sowing and treatment of sown cultivated areas, but before growth has occurred. For this purpose, tank mixes or ready formulations can be employed.

The present invention therefore also relates to a process for protecting crop plants against phytotoxic side effects of herbicides, wherein an effective amount of a compound of the formula I is applied before, after or at the same time as the herbicide.

The compounds of the formula I according to the invention can be applied in conventional formulations, if appropriate mixed with further active components or also together with a herbicide, as wettable powders, emulsifiable concentrates, sprayable solutions, dusts, dressings, dispersions, granules or microgranules.

Wettable powders are preparations which are uniformly dispersible in water and which contain, besides the active ingredient and, if appropriate, in addition to a diluent or inert substance, wetting agents, for example polyoxyethylated alkylphenoles, polyoxyethylated fatty alcohols or alkyl- or alkylphenylsulfonates, and dispersants, for example sodium ligninsulfonate, sodium 2,2'-dinaphthylmethane-6,6'-disulfonates, sodium dibutylnaphthalenesulfonate or sodium oleoylmethyltaurinate. They are prepared in a conventional fashion, for example by grinding and mixing the components.

Emulsifiable concentrates can be prepared, for example, by dissolving the active ingredient in an inert organic solvent, for example butanol, cyclohexanone, dimethylformamide, xylene or higher-boiling aromatics or hydrocarbons, with addition of one or more emulsifiers. In the case of liquid active ingredients, the solvent part can be omitted completely or partly. Emulsifiers which can be used are the following, for example: calcium salts of alkylarylsulfonic acids, such as Ca dodecylbenzenesulfonate, or nonionic emulsifiers, such as fatty acid polyglycol esters, alkylaryl polyglycol ethers, fatty alcohol polyglycol ethers, propylene oxide/ethylene oxide condensation products, alkyl polyglycol ethers, sorbitan fatty acid esters, polyoxyethylene sorbitan fatty acid esters or polyoxyethylene sorbitol esters.

Dusts are obtained by grinding the active ingredient with finely divided, solid substances, for example talc or natural clays, such as kaolin, bentonite, pyrophillite or diatomaceous earth.

Granules can be prepared either by atomizing the active ingredient onto adsorptive, granulated inert material or by applying the active ingredient concentrates onto the surface of excipients such as sand or kaolinites, or of granulated inert material, by means of binders, for example polyvinyl alcohol, sodium polyacrylate, or alternatively mineral oils. Suitable active ingredients can also be granulated in the fashion which is conventional for the preparation of fertilizer granules—if desired mixed with fertilizers.

In wettable powders, the active ingredient concentration is about 10 to 90% by weight; the remainder to 100% by weight comprises conventional formulation components. In the case of emulsifiable concentrates, the active ingredient concentration can be about 10 to 80% by weight. Dustable formulations usually contain 5 to 20% by weight of acative ingredient, and sprayable solutions about 1 to 20% by weight. In the case of granules, the active ingredient content depends partly on whether the active compound is present in liquid or solid form and on which granulation auxiliaries, fillers etc. are used.

In addition, the active ingredient formulations mentioned optionally contain the adhesives, wetting agents, dispersants, emulsifiers, penetrants, solvents, fillers or excipients which are conventional in each case.

For application, the concentrates, present in commercially available form, are diluted, if appropriate, in a conventional fashion, for example using water in the case of wettable powders, emulsifiable concentrates, dispersions and, in some cases, also in the case of microgranules. Dust-form and granulated formulations, and also sprayable solutions, are usually not further diluted with additional inert substances before application.

The application rates required for the compounds of the formula I when used as safeners can vary within broad limits depending on the indication and herbicide use, and generally vary between 0.01 and 10 kg of active ingredient per hectare.

The following examples serve to illustrate the invention.

A. Formulation examples (a) A dust is obtained by mixing 10 parts by weight of a compound of the formula I and 90 parts by weight of talc or inert substance and comminuting in a hammer mill.

(b) A wettable powder which is easily dispersible in water is obtained by mixing 25 parts by weight of a compound of the formula I, 64 parts by weight of kaolin-containing quartz as inert material, 10 parts by weight of potassium ligninsulfonate and 1 part by weight of sodium oleoylmethyltaurinate as wetting agent and dispersant and grinding in a pin disk mill.

(c) A dispersion concentrate which is easily dispersible in water is obtained by mixing 20 parts by weight of a compound of the formula I with 6 parts by weight of alkylphenol polyglycol ether ((R)Triton ×207), 3 parts by weight of isotridecanol polyglycol ether (8 EO) and 71 parts by weight of paraffinic mineral oil (boiling range, for example, about 255 to above 377° C.) and grinding in a ball mill to a fineness of below 5 microns.

(d) An emulsifiable concentrate is obtained from 15 parts by weight of the compound of the formula I, 75 parts by weight of cyclohexanone as solvent and 10 parts by weight of oxyethylated nonylphenol as emulsifier.

(e) A concentrate which is easily emulsified in water and which is made from a phenoxycarboxylic acid ester and an antidote (10:1) is obtained from 12.00% by weight of ethyl 2-[4-(6-chlorobenzoxazol-2-yloxy)-phenoxy]-propionate, 1.20% by weight of a compound of the formula I, 69.00% by weight of xylene, 7.80% by weight of calcium dodecylbenzenesulfonate, 6.00% by weight of ethoxylated nonylphenol (10 EO), and 4.00% by weight of ethoxylated castor oil (40 EO).

Formulation is carried out as specified under Example (a).

(f) A concentrate which is easily dispersible in water and which is made from a phenoxycarboxylic acid ester and an antidote (1:10) is obtained from 4.0% by weight of ethyl 2-[4-(6-chlorobenzoxazol2-yloxy)-phenoxyl]-propionate, 40.0% by weight of a compound of the formula I, 30.0% by weight of xylene, 20.0% by weight of cyclohexanone 4.0% by weight of calcium dodecylbenzenesulfonate, and 2.0% by weight of ethoxylated castor oil (40 EO).

B. Chemical examples

Examples 1 and 2.

Ethyl 1-phenylpyrazole-5-(and 3)-carboxylate.

15 g of ethyl vinyl ether were added dropwise to 14 g of ethyl chloroformylformate at between 0° and 30° C., and the mixture was stirred for a further 20 hours at 20°-30° C. The reaction mixture was concentrated in a water-pump vacuum, and the residue was taken up in 100 ml of glacial acetic acid. 10.8 g of phenylhydrazine in 150 ml of glacial acetic acid were added dropwise to this solution at between 10° and 80° C., and the mixture was refluxed for 2 hours. The product obtained was then introduced into 1 liter of water and extracted twice with 300 ml of ethyl acetate. The organic extract was washed once with 100 ml of water, twice with 100 ml of saturated NaHCO$_3$ solution and again with 100 ml of water and dried over Mg$_2$SO$_4$. After distillative separation, ethyl 1-phenylpyrazole-5-carboxylate, boiling point 100–102/0.5 torr (Example 1) and ethyl 1-phenyl-pyrazole-3-carboxylate, boiling point 125–128/0.5 torr (Example 2) were obtained. Yield: 10.5 g.

Example 3

1-Phenylpyrazole-5-carboxylic acid.

4.4 g of ethyl 1-phenylpyrazole-5-carboxylate from Example 1 were stirred for 6 hours at room temperature with 10 ml of 16.5% strength aqueous NaOH and 10 ml of ethanol; the ethanol was removed by distillation, the aqueous phase was extracted twice with 10 ml of toluene, and the pH was adjusted to 3 using concentrated HCl. The precipitate was filtered off under suction, washed with a little water and dried: 3.1 g of product of boiling point 182°–183° C. were obtained.

Example 4

Ethyl 1-(2,6-dichlorophenyl)-pyrazole-5-carboxylate.

145 g of ethyl vinyl ether were added dropwise to 137 g of ethyl chloroformylformate with cooling using ice/common salt; after warming to room temperature, the mixture was stirred for a further 20 hours. The volatile components were removed by distillation, and the residue was fractionated in a water-pump vacuum. Ethyl 4-ethoxy-2-oxobut-3-enoate of boiling point 140°–143° C./13 torr were obtained. 17.5 g of product were dissolved in 200 ml of toluene. 17.5 g of 2,6-dichlorophenylhydrazine were added at 0° C. were stirring. The mixture was slowly heated to boiling, and ethanol and water were removed in a water separator until the boiling point remained constant at 111° C. The residue was diluted with toluene, washed twice with 2 N hydrochloric acid, saturated hydrogen carbonate solution and water, dried, evaporated to dryness and recrystallized from ethanol. Yield: 18.3 g. Melting point: 51°–53° C.

Example 5

Ethyl 4-bromo-1-(2,6-dichlorophenyl)-pyrazole-5-carboxylate.

14.3 g of ethyl 1-(2,6-dichlorophenyl)-pyrazole-5-carboxylate from Example 4 were dissolved in 100 ml of glacial acetic acid, 10 g of Na acetate were added, and 4.5 g of bromine were added dropwise at room temperature. After 60 hours, the reaction mixture was poured into 1 liter of water, washed with water and recrystallized from ethanol. Yield: 8.2 g Melting point: 62°–65° C.

Examples 6 and 7

Cyclohexyl 1-(3-trifluoromethylphenyl)-pyrazole-5-(and 3)-carboxylate 15 g of ethyl vinyl ether were added dropwise to 19.5 g of cyclohexyl chloroformylformate at 0° C., the mixture wsa stirred at room temperature for 20 hours, and the volatile components were removed by distillation. 200 ml of toluene and 0.5 g of p-toluenesulfonic acid were added, and the mixture was heated for 2 hours on a water separator. A solution of 17.6 g of 3-trifluoromethylphenylhydrazine in 100 ml of toluene was added at 100° C., and the mixture was heated on a water separator until the distillate distilled over at a constant temperature of 111° C. The product was diluted with toluene, washed twice with 100 ml of 2 N HCl, twice with 100 ml of saturated NaHCO$_3$ solution and once with 100 ml of water and dried over MgSO$_4$, and the solution was evaporated to dryness. After column chromatography, cyclohexyl 1-(3-trifluoromethylphenyl)-pyrazole-5-carboxylate was obtained as a colorless oil, yield 8.2 g (Example 6), and cyclohexyl 1-(3-trifluoromethylphenyl)-pyrazole-3-carboxylate as an oil, yield 8.7 g (Example 7). The compounds were characterized by $^1$H NMR spectroscopy.

Examples 8 and 9

Methyl 1-(4-methylphenyl)-pyrazole-5(and 3)-carboxylate.

12.5 g of p-tolylhydrazine in 150 ml of glacial acetic acid were added to a solution of 16 g of methyl 4-ethoxy-2-oxobut-3-enoat in 100 ml of glacial acetic acid at 50° C. The mixture was stirred at 100° C. for 5 hours, poured into 1 liter of water, and extracted twice with 100 ml of ethyl acetate. The organic phase was washed with saturated NaHCO$_3$ solution and subsequently with water, and dried. After evaporating in a water-pump vaccum, the mixture was separated by distillation in a high vacuum. 4.1 g of methyl 1-(4-methylphenyl)-pyrazole-5-carboxylate of boiling point 116°–120° C./0.01 torr (example 8) and 5.3 g of methyl 1-(4-methylphenyl)-pyrazole-3-carboxylate of boiling point 138°–142° C./0.01 torr were obtained. The compounds were characterized by $^1$H NMR spectroscopy.

The compounds of the formula I shown in the table below are prepared by the procedure described in the examples above or are obtained by derivatization of the compounds described above.

TABLE I

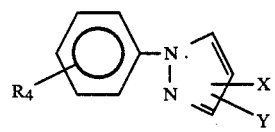

| Example No. | $R_n$ | 4-Y | X | m.p. (°C.) (b.p./torr) |
|---|---|---|---|---|
| 10 | H | H | 5-COOK | |
| 11 | H | H | 5-COONa | |

TABLE I-continued

[Structure: R_4-substituted phenyl-N-N-pyrazole with X and Y substituents]

| Example No. | $R_n$ | 4-Y | X | m.p. (°C.) (b.p./torr) |
|---|---|---|---|---|
| 12 | " | " | 5-COO$^\ominus$NH$^\oplus$(C$_2$H$_4$OH)$_3$ | 131–132 |
| 13 | " | " | 5-COO$^\ominus$NH$_3^\oplus$—c-C$_6$H$_11$ | |
| 14 | " | Br | 5-COOC$_2$H$_5$ | 59–61 |
| 15 | H | Br | 3-COOC$_2$H$_5$ | 75–87 |
| 16 | " | Br | 5-COO$^\ominus$H$_2^\oplus$N(piperidine) | Oil |
| 17 | H | Br | 5-COO$^\ominus$H$_2$N$^\oplus$—c-C$_6$H$_{11}$ | 139–143 |
| 18 | H | Cl | 5-COOC$_2$H$_5$ | |
| 19 | " | " | 5-COOH | |
| 20 | " | " | 5-COO—n-C$_{12}$H$_{25}$ | |
| 21 | " | H | 3-COOH | 142–144 |
| 22 | " | " | 3-COO$^\ominus$NH(C$_2$H$_4$OH)$_3$ | Oil |
| 23 | " | Br | 3-COOC$_2$H$_5$ | |
| 24 | " | " | 3-COOH | |
| 25 | " | " | 3-COOnC$_6$H$_{13}$ | |
| 26 | " | Cl | 3-COOCH$_3$ | 66–68 |
| 27 | " | " | 3-COOH | 174–175 |
| 28 | " | " | 3-COOK | |
| 29 | " | " | 3-COOCH$_2$CCl$_3$ | |
| 30 | 4-CH$_3$ | H | 5-COOH | 192–196 |
| 31 | 4-CH$_3$ | H | 3-COOH | 169–172 |
| 32 | " | Br | 5-COOC$_2$H$_5$ | |
| 33 | " | " | 3-COOC$_2$H$_5$ | |
| 34 | 2,4-Cl$_2$ | H | 5-COOC$_2$H$_5$ | 56–60 |
| 35 | " | " | 5-COOH | 212–213 |
| 36 | 2,4-Cl$_2$ | H | 3-COOH | 177–180 |
| 37 | " | " | 5-COSC$_2$H$_5$ | Oil |
| 38 | " | " | 5-CON(1,2,4-triazol-1-yl) | |
| 39 | " | Br | 5-COOC$_2$H$_5$ | 45–48 |
| 40 | " | " | 3-COOC$_2$H$_5$ | 91–102 |
| 41 | " | " | 3-COOH | 184–188 |
| 42 | " | " | 5-COOH | 175–177 |
| 43 | " | " | 5-COO$^\ominus$NH$^\oplus$(C$_2$H$_4$OH)$_3$ | 72–75 |
| 44 | " | " | 5-COOK | >260 |
| 45 | " | H | 3-COOC$_2$H$_5$ | 72–77 |
| 46 | " | H | 5-COOCH$_2$CF$_2$CFHCF$_3$ | Oil |
| 47 | " | " | 5-COO—n-C$_{12}$H$_{25}$ | Oil |
| 48 | " | " | 5-COO—c-C$_6$H$_{11}$ | Oil |
| 49 | " | " | 5-COO$^-$Li$^+$ | >260 |
| 50 | " | " | 3-COO$^-$K$^+$ | >260 |
| 51 | " | " | 5-COO$^-$Ca$_{\frac{1}{2}}^{2+}$ | 178–180 |
| 52 | " | " | 5-COO$^\ominus$NH$_4^\oplus$ | 140–143 |
| 53 | " | Br | 5-CONH$_2$ | 118–120 |
| 54 | " | H | 3-COO$^\ominus$NH$_4^\oplus$ | 212–215 |
| 55 | " | Br | 5-CN | 106–110 |
| 56 | " | " | 5-CO—N(phthalimido) | |
| 57 | " | " | 5-CONHCH$_2$CH$_2$OH | 49–50 |
| 58 | " | " | 5-COOCH$_2$SCH$_3$ | |

TABLE I-continued

| Example No. | $R_n$ | 4-Y | X | m.p. (°C.) (b.p./torr) |
|---|---|---|---|---|
| 59 | " | Cl | 5-C(=N-N=N-NH) (tetrazol-5-yl) | |
| 60 | " | " | 3-C(=N)-O-CH$_2$-C(CH$_3$)$_2$ (4,4-dimethyl-oxazolin-2-yl) | |
| 61 | 2,4-Cl$_2$ | Cl | 5-C(=N)-O-N=C(CH$_3$) (5-methyl-1,2,4-oxadiazol-3-yl) | |
| 62 | 2,6-(CH$_3$)$_2$ | H | 5-COOH | 167–170 |
| 63 | " | " | 5-COOC$_2$H$_5$ | 101–108/0.02 |
| 64 | " | " | 3-COO$^\ominus$ $^+$NH(C$_2$H$_4$OH)$_3$ | 83–86 |
| 65 | " | " | 3-COO$^\ominus$H$_3$N$^\oplus$—c-C$_6$H$_{11}$ | 144–146 |
| 66 | " | Br | 5-C(=NH)(NHOH) | |
| 67 | " | Br | 5-COOCH$_2$—CF$_2$CHFCF$_3$ | |
| 68 | " | Cl | 5-COOH | |
| 69 | " | Cl | 5-C(=NH)(NHOH) | |
| 70 | 2,6-(C$_2$H$_5$)$_2$ | H | 5-COOC$_2$H$_5$ | 119–123/0.01 |
| 71 | " | H | 3-COOC$_2$H$_5$ | 135–152/0.01 |
| 72 | " | H | 5-COOH | 142–146 |
| 73 | " | H | 3-COOH | 162–164 |
| 74 | " | Br | 5-COOH | 117–123 |
| 75 | " | " | 3-COOH | 136–141 |
| 76 | " | " | 5-CONH$_2$ | |
| 77 | " | Br | 3-CONHOH | |
| 78 | " | " | 5-C(=O)ONC$_2$H$_4$ | |
| 79 | " | Cl | 5-COOH | |
| 80 | " | Cl | 3-COOH | |
| 81 | " | Cl | 5-COO—n-C$_{12}$H$_{25}$ | |
| 82 | 2-CH$_3$,6-C$_2$H$_5$ | H | 5-COOC$_2$H$_5$ | 120–125/0.02 |
| 82 | " | " | 3-COOC$_2$H$_5$ | 140–144/0.02 |
| 83 | " | " | 5-COOH | 126–128 |
| 84 | " | " | 5-COO$^-$H$_2$N$^+$(cyclohexyl) | 137–140 |
| 85 | 2-CH$_3$,6-C$_2$H$_5$ | Br | 5-COOH | |
| 86 | " | Cl | 5-COOC$_2$H$_5$ | |
| 87 | " | " | 3-COOH | |
| 88 | 2,6-Cl$_2$ | H | 5-COOH | 207–208 |
| 89 | " | Br | 5-COOH | 187–192 |
| 90 | " | H | 5-CONH$_2$ | 117–118 |

TABLE I-continued

| Example No. | $R_n$ | 4-Y | X | m.p. (°C.) (b.p./torr) |
|---|---|---|---|---|
| 91 | " | H | 5-CONH-(2-F, 4-Cl, 5-OCH₃-phenyl) | 225 |
| 92 | " | " | 5-COSC₂H₅ | Oil |
| 93 | " | " | 5-COO(CH₂)₂(CF₂)₅—CF₃ | 57–61 |
| 94 | " | " | 5-COO—n-C₁₂H₂₅ | 44–48 |
| 95 | " | " | 5-COOCH₃ | 113–115 |
| 96 | " | " | 5-CN | 94–96 |
| 97 | " | " | 5-CONHCH₃ | 220–223 |
| 98 | 2,6-Cl₂,3-NO₂ | " | 5-COOC₂H₅ | Oil |
| 99 | " | " | 5-COOH | 178–179 |
| 100 | 2,6-Cl₂ | " | 5-CNHNH-(2-F, 4-Cl, 5-OCH₃-phenyl) | 176–177 |
| 101 | " | " | 5-C(=NH)NHOH | |
| 102 | " | " | 5-C(=O)O—N=C(CH₃)₂ | |
| 103 | " | " | 5-C(oxadiazole with CH₃) | |
| 104 | " | Br | 5-COOC₂H₅ | |
| 105 | " | Br | 5-COOCH₂CF₂CHFCF₃ | |
| 106 | " | " | 5-C(=O)—NHSO₂CH₃ | |
| 107 | 2,6-Cl₂ | Br | 5-C(benzimidazole) | |
| 108 | " | Cl | 5-COOC₂H₅ | |
| 109 | " | Cl | 5-COOH | |
| 110 | " | Cl | 5-(1H-tetrazol-5-yl) | |

TABLE I-continued

| Example No. | $R_n$ | 4-Y | X | m.p. (°C.) (b.p./torr) |
|---|---|---|---|---|
| 111 | " | " | 5-C(=O)-N-phthalimide | |
| 112 | " | H | 3-COOH | |
| 113 | " | Br | 3-COOC$_2$H$_5$ | |
| 114 | " | Cl | 3-COOCH$_3$ | |
| 115 | 3,4-Cl$_2$ | H | 5-COOC$_2$H$_5$ | 95–99 |
| 116 | " | " | 3-COOC$_2$H$_5$ | 93–96 |
| 117 | " | " | 5-COOH | 217–219 |
| 118 | " | " | 5-COO$^\ominus$NH$^\oplus$(C$_2$H$_4$OH)$_3$ | 137–140 |
| 119 | " | Br | 5-COONC(CH$_3$)$_2$ | |
| 120 | " | Cl | 5-COOCH$_3$ | |
| 121 | " | " | 3-COOC$_2$H$_5$ | |
| 122 | " | " | 5-COOnC$_{12}$H$_{25}$ | |
| 123 | 3,5-Cl$_2$ | H | 5-COOC$_2$H$_5$ | 94–97 |
| 124 | " | " | 5-COOH | 229–232 |
| 125 | " | Br | 5-COOH | |
| 126 | " | " | 3-COOH | |
| 127 | " | Cl | 5-COOC$_2$H$_5$ | |
| 128 | 2,3,4-Cl$_3$ | H | 5-COOC$_2$H$_5$ | Oil |
| 129 | " | H | 5-COOH | 146 |
| 130 | " | " | 3-COOC$_2$H$_5$ | Oil |
| 131 | " | Br | 5-COOH | |
| 132 | " | " | 5-COOCH$_2$CF$_2$CHFCF$_3$ | — |
| 133 | 2,3,4-Cl$_3$ | Br | 5-COOCH$_2$CCl$_3$ | |
| 134 | " | Cl | 5-COOH | |
| 135 | 2,4,6-Cl$_3$ | H | 5-COOC$_2$H$_5$ | 99–101 |
| 136 | " | " | 3-COOC$_2$H$_5$ | 114–115 |
| 137 | " | " | 5-COOH | |
| 138 | " | " | 3-COOH | |
| 139 | " | " | 5-COOCH$_3$ | |
| 140 | " | Br | 5-COOH | |
| 141 | " | Br | 3-COOH | |
| 142 | " | Cl | 5-COOH | |
| 143 | " | " | 3-COOH | |
| 144 | 4-C$_6$H$_5$ | H | 5-COOC$_2$H$_5$ | 40–43 |
| 145 | " | " | 3-COOC$_2$H$_5$ | 89–92 |
| 146 | " | " | 3-COOH | 196–199 |
| 147 | " | H | 5-COOnC$_{12}$H$_{25}$ | |
| 148 | " | Br | 5-COOH | |
| 149 | " | Br | 3-COOH | |
| 150 | " | Cl | 5-COOH | |
| 151 | " | " | 3-COOH | |
| 152 | 2-Cl | H | 5-COOCH$_3$ | 64–70 |
| 153 | " | " | 5-COOC$_2$H$_5$ | Oil |
| 154 | " | " | 5-COOH | 157–161 |
| 155 | " | " | 5-CONH$_2$ | |
| 156 | " | " | 5-CONHC$_2$H$_5$ | |
| 157 | " | " | 5-CONHNHC$_2$H$_5$ | |
| 158 | " | " | 5-COSC$_2$H$_5$ | |
| 159 | " | " | 5-COO—nC$_{12}$H$_{25}$ | |
| 160 | " | " | 3-COOC$_2$H$_5$ | |
| 161 | " | " | 3-COSC$_2$H$_5$ | |
| 162 | " | " | 3-COOH | |
| 163 | " | " | 3-COOnC$_4$H$_9$ | |
| 164 | " | Br | 5-COOC$_2$H$_5$ | Oil |
| 165 | 2-Cl | Br | 5-COSC$_2$H$_5$ | |
| 166 | " | " | 5-COOH | |
| 167 | " | " | 3-COOC$_2$H$_5$ | |
| 168 | " | Cl | 5-COOC$_2$H$_5$ | |
| 169 | " | Cl | 5-COOH | |
| 170 | " | " | 3-COOC$_2$H$_5$ | |
| 171 | " | " | 3-COSC$_2$H$_5$ | |
| 172 | 2,4-Cl$_2$—5-OCH$_3$ | H | 5-COOC$_2$H$_5$ | Oil |
| 173 | " | " | 5-COOH | 187–190 |
| 174 | " | " | 3-COOC$_2$H$_5$ | |

TABLE I-continued

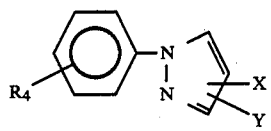

| Example No. | $R_n$ | 4-Y | X | m.p. (°C.) (b.p./torr) |
|---|---|---|---|---|
| 175 | " | Br | 5-COSC$_2$H$_5$ | |
| 176 | " | Cl | 3-COOC$_2$H$_5$ | |
| 177 | " | " | 5-COOC$_2$H$_5$ | |
| 178 | 2,4-Cl$_2$—5-CO$_2$C$_2$H$_5$ | H | 5-COOC$_2$H$_5$ | 170–175/0.01 |
| 179 | " | " | 5-COOCH$_3$ | |
| 180 | " | " | 5-COO—c-C$_6$H$_{11}$ | |
| 181 | " | " | 3-COOC$_2$H$_5$ | |
| 182 | " | Br | 5-COOC$_2$H$_5$ | |
| 183 | " | Cl | 5-COOC$_2$H$_5$ | |
| 184 | 2-F—4-Cl—5-OCH$_3$ | H | 5-COOC$_2$H$_5$ | 155–162/0.01 |
| 185 | " | " | 5-COOH | 207–210 |
| 186 | " | " | 5-CN | |
| 187 | " | " | 5-CONH$_2$ | |
| 188 | " | " | 5-CNHNH$_2$ | |
| 189 | " | " | 3-COOC$_2$H$_5$ | |
| 190 | " | " | 3-COOH | |
| 191 | " | " | 5-COONH$_4$ | |
| 192 | " | " | 5-COOK | |
| 193 | " | Cl | 5-COOCH$_3$ | |
| 194 | " | Cl | 5-COOH | |
| 195 | " | " | 3-COOCH$_3$ | |
| 196 | " | Br | 5-COOC$_4$H$_9$ | |
| 197 | " | Br | 5-COOCH$_2$CCH | |
| 198 | 2-F—4-Cl—5-OCH$_3$ | Br | 3-COOC$_2$H$_5$ | |
| 199 | 4-CF$_3$ | H | 5-COOC$_2$H$_5$ | 53–54 |
| 200 | " | " | 3-COOC$_2$H$_5$ | 79–84 |
| 201 | 4-CF$_3$—2,6-(NO$_2$)$_2$ | H | 5-COOC$_2$H$_5$ | 108–112 |
| 202 | " | " | 3-COOC$_2$H$_5$ | 138–142 |
| 203 | 2,Cl—4CF$_3$ | H | 5-COOC$_2$H$_5$ | 45–47 |
| 204 | " | " | 5-COOH | 149–150 |
| 205 | " | " | 3-COOC$_2$H$_5$ | 66–69 |
| 206 | 3-CF$_3$ | H | 5-COOC$_2$H$_5$ | 87–101/0.01 |
| 207 | " | " | 3-COOC$_2$H$_5$ | 79–84 |
| 208 | " | " | 5-COOH | 136–138 |
| 209 | " | " | 3-COO$^-$(Ca$^{2+}$)$_{\frac{1}{2}}$ | 244–261 |
| 210 | " | " | 3-COOK | 242 |
| 211 | " | " | 3-COONa | 283 |
| 212 | " | " | 5-COO$^-$Ca$^{2+}$$_{\frac{1}{2}}$ | 128–131 |
| 213 | " | " | 3-COO—c-C$_6$H$_{11}$ | 67–68 |
| 214 | " | Br | 3-COO—C—C$_6$H$_{11}$ | 86–91 |
| 215 | " | H | 5-COO—c-C$_6$H$_{11}$ | 155–160/0.5 |
| 216 | " | Br | 5-COO—c-C$_6$H$_{11}$ | Oil |
| 217 | " | H | 5-COO$^-$K$^+$ | 208–213 |
| 218 | " | " | 5-COO$^-$NH$_4^+$ | 65–71 |
| 219 | " | " | 3-COO$^-$NH$_4^+$ | 207–212 |
| 220 | " | " | 3-COO$^-$Li$^+$ | >250 |
| 221 | " | " | 5-CONH—4-C$_6$H$_4$—4-Cl | |
| 222 | " | " | 5-C(NH$_2$)NOCH$_3$ | |
| 223 | " | " | 5-COOCH$_2$CH$_2$c-C$_6$H$_{11}$ | |
| 224 | " | " | 5-CSOC$_2$H$_5$ | |
| 225 | " | " | 3-COSC$_2$H$_5$ | |
| 226 | " | Br | 5-COSC$_2$H$_5$ | |
| 227 | " | Br | 3-COSC$_2$H$_5$ | |
| 228 | " | Cl | 5-COONHCOCH$_3$ | |
| 229 | " | Cl | 5-COO(CH$_2$)$_2$OC$_2$H$_2$CH$_3$ | |
| 230 | " | " | 5-COOCH$_2$C$_6$H$_5$ | |
| 231 | 2,4-F$_2$ | H | 5-COOC$_2$H$_5$ | 102–106/0.02 |
| 232 | " | " | 3-COOC$_2$H$_5$ | 120–122/0.02 |
| 233 | " | " | 5-COOH | 196–199 |
| 234 | " | Br | 5-COOH | 165–168 |
| 235 | " | Br | 3-COOC$_2$H$_5$ | |
| 236 | " | Cl | 5-COOH | |
| 237 | 4-F | H | 5-COOC$_2$H$_5$ | 96–98 |
| 238 | 4-F | H | 3-COOC$_2$H$_5$ | 44–49 |
| 239 | " | H | 5-COOH | 147–148 |
| 240 | " | H | 5-COSC$_2$H$_5$ | 62–65 |
| 241 | " | " | 5-CSSC$_2$H$_5$ | |
| 242 | " | " | 5-CSN(CH$_3$)$_2$ | |
| 243 | " | " | 5-CONHNHCOC$_6$H$_5$ | |
| 244 | " | " | 3-COSC$_2$H$_5$ | |
| 245 | " | " | 3-CCNH$_2$ | |
| 246 | " | Br | 5-COOH | 207 (decomp.) |

TABLE I-continued

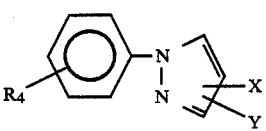

| Example No. | $R_n$ | 4-Y | X | m.p. (°C.) (b.p./torr) |
|---|---|---|---|---|
| 247 | " | Br | 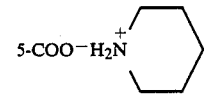 5-CO-N-triazole | |
| 248 | " | Br | 3-COOC$_2$H$_5$ | 79–83 |
| 249 | " | Cl | 5-COOH | |
| 250 | " | " | 3-COOH | |
| 251 | 4Br | H | 5-COOC$_2$H$_5$ | 63–65 |
| 252 | " | " | 5-COOC$_2$H$_5$ | 78–81 |
| 253 | " | " | 5-COOH | |
| 254 | " | " | 5-COSC$_2$H$_5$ | |
| 255 | " | " | 3-COSC$_2$H$_5$ | |
| 256 | " | Br | 5-COOH | |
| 257 | " | Cl | 5-COOH | |
| 258 | " | " | 3-COOH | |
| 259 | 4-Cl | H | 5-COOC$_2$H$_5$ | 60–65 |
| 260 | " | " | 3-COOH | 169–174 |
| 261 | 4-Cl | H | 5-COOH | 181–182 |
| 262 | " | " | 3-COOC$_2$H$_5$ | 71–74 |
| 263 | " | Br | 3-COOC$_2$H$_5$ | 107–109 |
| 264 | " | " | 5-COOC$_2$H$_5$ | 109–112 |
| 265 | " | H | 5-COO$^-$H$_2$N$^+$-piperidinium | 152–154 |
| 266 | " | " | 5-COO$^-$H$_3$N$^+$-(2,6-dimethylcyclohexyl) | Oil |
| 267 | " | Br | 5-COOH | 196–198 |
| 268 | " | " | 5-COO$^-$HN$^+$(C$_2$H$_4$OH)$_3$ | 112–114 |
| 269 | " | " | 5-COO$^-$H$_2$N$^+$-(2,4,6-trimethylcyclohexyl) | Oil |
| 270 | 3-Cl | H | 5-COOC$_2$H$_5$ | 55–60 |
| 271 | " | " | 5-COOH | 205 |
| 272 | 3-Cl—5-NO$_2$ | H | 5-COOC$_2$H$_5$ | 104–116 |
| 273 | " | " | 3-COOC$_2$H$_5$ | 141–147 |
| 274 | 3-Cl | H | 3-COOH | |
| 275 | " | " | 3-COSC$_2$H$_5$ | |
| 276 | " | Br | 5-COOCH$_3$ | |
| 277 | " | Cl | 5-COOH | |
| 278 | " | " | 3-COOH | |
| 279 | 3-COOC$_2$H$_5$ | H | 3-COOC$_2$H$_5$ | 92–95 |
| 280 | " | " | 5-COOC$_2$H$_5$ | 85–87 |
| 281 | 3-COO$^-$HN$^+$(C$_2$H$_4$OH)$_3$ | H | 3-COO$^-$HN$^+$(C$_2$H$_4$OH)$_3$ | Oil |
| 282 | 3-COOH | H | 5-COOH | 236–238 |
| 283 | 3-COOH | H | 3-COOH | 240–243 |
| 284 | 4-COOH | H | 5-COOH | >260 |
| 285 | " | " | 3-COOH | >260 |
| 286 | 3-OCF$_2$CHF$_2$ | H | 5-COO—c-C$_6$H$_{11}$ × H$_2$SO$_4$ | Oil |
| 287 | " | " | 5-COOC$_2$H$_5$ | Oil |
| 288 | " | H | 3-COOC$_2$H$_5$ | 47–51 |
| 289 | " | " | 5-COO—c-C$_6$H$_{11}$ | Oil |
| 290 | " | " | 3-COO—c-C$_6$H$_{11}$ | Oil |

TABLE I-continued

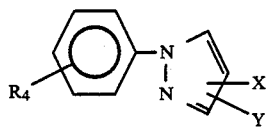

| Example No. | $R_n$ | 4-Y | X | m.p. (°C.) (b.p./torr) |
|---|---|---|---|---|
| 291 | 3-OCF$_2$CHF$_2$ | H | 5-COO—i-borneyl | Oil |
| 292 | " | " | 3-COO—i-borneyl | 88–90 |
| 293 | " | Br | 5-COO—c-C$_6$H$_{11}$ | Oil |
| 294 | " | " | 3-COOC$_2$H$_5$ | 62–64 |
| 295 | " | " | 5-COOC$_2$H$_5$ | Oil |
| 296 | " | Cl | 5-COOC$_2$H$_5$ | |
| 297 | " | " | 3-COOC$_2$H$_5$ | |
| 298 | 3-OCF$_2$CHFCF$_3$ | H | 5-COOC$_2$H$_5$ | Oil |
| 299 | " | " | 5-COOH | 129–131 |
| 300 | " | " | 5-COSC$_2$H$_5$ | |
| 301 | " | H | 5-CN | |
| 302 | " | " | 3-COOC$_2$H$_5$ | 44–46 |
| 303 | " | " | 3-COOH | 104 (decomp.) |
| 304 | " | H | 3-COSC$_2$H$_5$ | |
| 305 | " | Br | 5-COOC$_2$H$_5$ | |
| 306 | " | " | 3-COOC$_2$H$_5$ | |
| 307 | 3-OCF$_3$ | H | 5-COOC$_2$H$_5$ | Oil |
| 308 | " | H | 3-COOC$_2$H$_5$ | 55–58 |
| 309 | " | Cl | 5-COOC$_2$H$_5$ | |
| 310 | 4-OCF$_3$ | H | 5-COOC$_2$H$_5$ | Oil |
| 311 | " | H | 5-COOH | 157–158 |
| 312 | " | " | 3-COOC$_2$H$_5$ | 68–71 |
| 313 | " | Cl | 5-COOC$_2$H$_5$ | 98–99 |
| 314 | 3-NO$_2$ | H | 5-COOC$_2$H$_5$ | 76–82 |
| 315 | 3-OCHF$_2$ | H | 5-COOC$_2$H$_5$ | |
| 316 | " | " | 5-COOH | |
| 317 | 2,4-F$_2$, 3,5-Cl$_2$ | H | 5-COOC$_2$H$_5$ | |
| 318 | " | " | 3-COOC$_2$H$_5$ | |
| 319 | " | " | 5-COOH | |
| 320 | " | Br | 5-COOC$_2$H$_5$ | |
| 321 | " | Cl | 3-COOC$_2$H$_5$ | |
| 322 | 4-O—C$_6$H$_5$ | H | 5-COOC$_2$H$_5$ | |
| 323 | " | " | 5-COOH | |
| 324 | 4-O—C$_6$H$_5$ | H | 3-COOC$_2$H$_5$ | |
| 325 | 4-O—C$_6$H$_4$—2-Cl | H | 5-COOC$_2$H$_5$ | |
| 326 | 4-NH$_2$ | H | 3-COOC$_2$H$_5$ | 84–87 |
| 327 | 3-NHCOCH$_3$ | H | 5-COOC$_2$H$_5$ | |
| 328 | 3-SH | H | 5-CQOC$_2$H$_5$ | |
| 329 | 3-S—C$_6$H$_5$ | H | 5-COOC$_2$H$_5$ | |
| 330 | 3-SO$_2$—C$_6$H$_5$ | H | 5-COOCH$_3$ | |
| 331 | 2,6-Cl$_2$—4-CF$_3$ | H | 5-COOC$_2$H$_5$ | 69–71 |
| 332 | " | H | 5-CONH$_2$ | 171–173 |
| 333 | " | H | 5-CN | 67–69 |
| 334 | " | H | 3-COOC$_2$H$_5$ | 112–115 |
| 335 | 4-NO$_2$ | H | 3-COOC$_2$H$_5$ | 159–161 |
| 336 | 3-C$_2$H$_5$ | H | 5-COOC$_2$H$_5$ | Oil |
| 337 | " | H | 3-COOC$_2$H$_5$ | Oil |
| 338 | 3-OCF$_3$ | H | 5-COOH | 113–115 |
| 339 | 4-OCF$_3$ | Br | 3-COOC$_2$H$_5$ | 92–97 |
| 340 | 4-F—3-NO$_2$ | H | 5-COOC$_2$H$_5$ | 74–76 |
| 341 | " | H | 5-COOH | 178 decomp. |
| 342 | 2,4,6-Cl$_3$ | Br | 5-COOC$_2$H$_5$ | 64–65 |
| 343 | 2,4,6-Cl$_3$—3-CH$_3$ | H | 5-COOC$_2$H$_5$ | 38–42 |
| 344 | 3-F— | H | 5-COOC$_2$H$_5$ | Oil |
| 345 | 3-F | H | 3-COOC$_2$H$_5$ | Oil |
| 346 | 2-CF$_3$ | H | 5-COOC$_2$H$_5$ | Oil |
| 347 | " | H | 5-COOH | 130–132 |
| 348 | 2-Cl—5-CF$_3$ | H | 5-COOC$_2$H$_5$ | Oil |
| 349 | " | H | 3-COOC$_2$H$_5$ | Oil |
| 350 | 3,5-(CF$_3$)$_2$ | H | 5-COOC$_2$H$_5$ | 63–67 |
| 351 | " | H | 3-COOC$_2$H$_5$ | 108–110 |
| 352 | " | H | 5-COOH | 124–126 |
| 353 | 2,4-Cl$_2$—6-CH$_3$ | H | 5-COOC$_2$H$_5$ | 63–65 |
| 354 | F$_5$ | H | 5-COOC$_2$H$_5$ | Oil |
| 355 | " | H | 3-COOC$_2$H$_5$ | Oil |
| 356 | " | H | 5-COOH | 146–150 |
| 357 | 4-NHCH=C(CN)$_2$ | H | 3-COOC$_2$H$_5$ | >220 |

TABLE I-continued

| Example No. | $R_n$ | 4-Y | X | m.p. (°C.) (b.p./torr) |
|---|---|---|---|---|
| 358 | 4-N(cyclohexene-dicarboximide) | H | 3-COOC$_2$H$_5$ | 115–117 |
| 359 | 3-NHCOCOOC$_2$H$_5$ | H | 5-COOC$_2$H$_5$ | 50–54 |
| 360 | 2,4-Cl$_2$—5NO$_2$ | Br | 5-CONH$_2$ | 204–206 |
| 361 | 2,3,6-Cl$_3$—3NO$_2$ | H | 5-COOC$_2$H$_5$ | 94–101 |
| 362 | '' | H | 5-COOH | 185–187 |
| 363 | '' | H | 5-COOK | 189–192 |
| 364 | 3-CF$_3$ | H | 5-CON(C$_2$H$_5$)$_2$ | 66–68 |
| 365 | '' | H | 5-CONHCH$_2$CH(OCH$_3$)$_2$ | 92–94 |
| 366 | '' | H | 5-CONH$_2$ | 119–121 |
| 367 | '' | H | 5-CONHCH$_3$ | 72–77 |
| 368 | '' | H | 5-CONHCH$_2$CH(C$_2$H$_5$)—n-C$_4$H$_9$ | Oil |
| 369 | '' | H | 5-CONH—c-C$_6$H$_{11}$ | 134 decomp. |
| 370 | 2-Cl—4-CF$_3$ | Br | 5-COOC$_2$H$_5$ | Oil |
| 371 | '' | Br | 3-COOC$_2$H$_5$ | 38–41 |
| 372 | '' | H | 5-COO—C$_6$H$_4$—OCH(CH$_3$)COOC$_2$H$_5$ | Oil |
| 373 | '' | H | 5-COO—C$_6$H$_4$—OCH(CH$_3$)COOH | 104–106 |
| 374 | 2-Cl—5-NO$_2$ | H | 5-COOC$_2$H$_5$ | 78–82 |
| 375 | 2-Cl | H | 5-CO(benzimidazol-1-yl) | 117–121 |
| 376 | '' | H | 5-CON(morpholino) | 125–126 |
| 377 | 5-NO$_2$—2-SC$_6$H$_5$ | H | 5-COOC$_2$H$_5$ | Oil |
| 378 | 5-Cl—2-NO$_2$ | H | 5-COOC$_2$H$_5$ | 90–94 |
| 379 | 3-Cl—4-NO$_2$ | H | 5-COOC$_2$H$_5$ | 109–113 |
| 380 | 2,4-(SC$_6$H$_5$)$_2$—5-NO$_2$ | H | 5-COOCH$_3$ | 145–148 |
| 381 | 4-O—CH$_3$ | H | 5-COOC$_2$H$_5$ | Oil |
| 382 | '' | H | 3-COOC$_2$H$_5$ | Oil |
| 383 | '' | H | 5-COOH | 170–172 |
| 384 | '' | H | 3-COOH | 185–187 |
| 385 | 2,3,5,6-F$_4$ | H | 5-COOC$_2$H$_5$ | 57–60 |
| 386 | '' | H | 5-COOH | 128–130 |
| 387 | '' | H | 5-CON(C$_2$H$_5$)$_2$ | 80–83 |
| 388 | '' | H | 5-COO—n-C$_6$H$_{13}$ | Oil |
| 389 | 3-N(cyclohexene-dicarboximide) | H | 5-COOC$_2$H$_5$ | 96–101 |
| 390 | 3-NO$_2$—4-OC$_6$H$_5$ | H | 5-COOC$_2$H$_5$ | 52–54 |
| 391 | '' | H | 5-COOH | 178–181 |
| 392 | 4-NH—SO$_2$CH$_3$ | H | 3-COOC$_2$H$_5$ | 150–155 |
| 393 | 3-Cl—4-F | H | 5-COOC$_2$H$_5$ | 84–87 |
| 394 | '' | H | 3-COOC$_2$H$_5$ | 122–125 |
| 395 | '' | H | 5-COOH | >225 |

TABLE I-continued

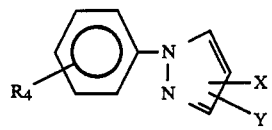

| Example No. | $R_n$ | 4-Y | X | m.p. (°C.) (b.p./torr) |
|---|---|---|---|---|
| 396 | 4-F—3-$CF_3$ | " | 3-$COOC_2H_5$ | 24–29 |
| 397 | 4-$N(CH_3)_2$—3-$CF_3$ | H | 5-$COOC_2H_5$ | Oil |
| 398 | " | H | 3-$COOC_2H_5$ | Oil |
| 399 | 3-Cl—2,6-$(C_2H_5)$ | H | 5-$COOC_2H_5$ | Oil |
| 400 | " | H | 3-$COOC_2H_5$ | Oil |
| 401 | " | H | 5-COOH | 145–147 |
| 402 | " | Br | 5-$COOC_2H_5$ | Oil |
| 403 | 2,4-$Br_2$ | H | 5-$COOC_2H_5$ | Oil |
| 404 | " | H | 3-$COOC_2H_5$ | 103–105 |
| 405 | " | H | 5-COOH | 217–219 |
| 406 | " | Br | 5-$COOC_2H_5$ | Oil |
| 407 | 2,4-$Cl_2$ | H | 3-$CONHSO_2CH_3$ | 155–159 |
| 408 | " | H | 3-$COOCH_3$ | 105–107 |
| 409 | " | H | 3-$COOCH_2C{\equiv}CH$ | 101–103 |
| 410 | " | H | 5-$COOCH_2C{\equiv}CH$ | Oil |
| 411 | " | H | 5-$COOCH(CH_3)_2$ | Oil |
| 412 | " | H | 5-$COOCH_2CCl_3$ | Oil |
| 413 | " | H | 5-$COONC(CH_3)_2$ | 87–89 |
| 414 | " | H | 5-$COOCH(CF_3)_2$ | Oil |
| 415 | " | H | 5-CN | 70–71 |
| 416 | " | H | 5-$COOCH_2Si(CH_3)_3$ | Oil |
| 417 | " | H | 3-$COOCH_2Si(CH_3)_3$ | 51–54 |
| 418 | " | H | 5-CON⟨morpholino⟩ | Oil |

Biological examples

A. Growth regulation

1. Growth inhibition in cereals

In dish experiments in a greenhouse, young cereal plants (wheat, barley and rye) at the 3-leaf stage were sprayed with compounds according to the invention at various active ingredient concentrations (kg/ha) until dripping wet.

When untreated control plants had reached a growth height of about 55 cm, the increase in growth in all plants was measured and the growth inhibition calculated in % of additional growth of the control plants. In addition, the phytotoxic action of the compounds was observed, 100% denoting cessation of growth and 0% denoting growth corresponding to the untreated control plants. It was apparent that the compounds have very good growth-regulating properties. The results are collated in the following table.

TABLE

| Compounds according to Ex. No. | Application conc., kg/ha | Growth inhibition (%) Wheat | Barley | Rye | Phytotoxic action |
|---|---|---|---|---|---|
| 17 | 2.5 | 15 | 22 | 19 | no |
|  | 1.25 | 11 | 16 | 14 | damage |
| 34 | " | 14 | 21 | 17 | no |
|  | " | 10 | 14 | 11 | damage |
| 42 | " | 25 | 38 | 22 | no |
|  | " | 22 | 23 | 17 | damage |
| 43 | " | 24 | 38 | 23 | no |
|  | " | 21 | 22 | 16 | damage |
| 44 | " | 24 | 37 | 23 | no |
|  | " | 20 | 23 | 17 | damage |
| 52 | " | 22 | 31 | 21 | no |
|  | " | 18 | 26 | 17 | damage |
| 53 | " | 16 | 21 | 19 | no |
|  | " | 10 | 15 | 13 | damage |
| 55 | " | 14 | 20 | 21 | no |
|  | " | 9 | 13 | 14 | damage |
| 62 | " | 18 | 21 | 14 | no |
|  | " | 14 | 15 | 12 | damage |
| 72 | " | 14 | 17 | 14 | no |
|  | " | 12 | 15 | 9 | damage |
| 83 | " | 19 | 22 | 19 | no |
|  | " | 12 | 14 | 13 | damage |
| 88 | " | 23 | 36 | 29 | no |
|  | " | 18 | 28 | 20 | damage |
| 89 | " | 26 | 39 | 24 | no |
|  | " | 21 | 24 | 19 | damage |
| 90 | " | 14 | 21 | 18 | no |
|  | " | 10 | 16 | 13 | damage |
| 92 | " | 17 | 22 | 19 | no |
|  | " | 11 | 17 | 14 | damage |
| 115 | 2.5 | 16 | 21 | 19 | no |
|  | 1.25 | 11 | 17 | 14 | damage |
| 116 | " | 17 | 22 | 19 | no |
|  | " | 12 | 17 | 13 | damage |
| 117 | " | 19 | 24 | 21 | no |
|  | " | 14 | 19 | 16 | damage |
| 128 | " | 16 | 21 | 17 | no |
|  | " | 11 | 16 | 13 | damage |
| 129 | " | 22 | 31 | 22 | no |
|  | " | 18 | 25 | 19 | damage |
| 135 | " | 15 | 19 | 18 | no |
|  | " | 11 | 16 | 14 | damage |
| 140 | " | 20 | 24 | 22 | no |
|  | " | 14 | 19 | 17 | damage |
| 153 | " | 20 | 23 | 21 | no |
|  | " | 13 | 19 | 16 | damage |
| 154 | " | 22 | 27 | 24 | no |
|  | " | 15 | 23 | 19 | damage |

TABLE-continued

| Compounds according to Ex. No. | Application conc., kg/ha | Growth inhibition (%) Wheat | Barley | Rye | Phytotoxic action |
|---|---|---|---|---|---|
| 178 | " | 14 | 19 | 19 | no |
|  | " | 12 | 14 | 15 | damage |
| 185 | " | 13 | 18 | 15 | no |
|  | " | 9 | 13 | 9 | damage |
| 204 | " | 16 | 19 | 17 | no |
|  | " | 11 | 16 | 15 | damage |
| 206 | " | 15 | 20 | 18 | no |
|  | " | 13 | 13 | 14 | damage |
| 208 | " | 20 | 35 | 22 | no |
|  | " | 14 | 24 | 17 | damage |
| 217 | " | 17 | 27 | 22 | no |
|  | " | 14 | 22 | 17 | damage |
| 218 | " | 18 | 27 | 19 | no |
|  | " | 15 | 23 | 16 | damage |
| 246 | " | 25 | 38 | 27 | no |
|  | " | 21 | 29 | 24 | damage |
| 267 | " | 21 | 30 | 22 | no |
|  | " | 17 | 23 | 17 | damage |
| 269 | " | 24 | 37 | 27 | no |
|  | " | 21 | 28 | 23 | damage |
| 295 | 2.5 | 19 | 29 | 22 | no |
|  | 1.25 | 16 | 24 | 17 | damage |
| 356 | " | 19 | 28 | 21 | no |
|  | " | 15 | 22 | 16 | damage |
| 366 | " | 17 | 21 | 17 | no |
|  | " | 11 | 16 | 13 | damage |
| 405 | " | 24 | 37 | 23 | no |
|  | " | 21 | 28 | 18 | damage |
| 413 | " | 19 | 26 | 18 | no |
|  | " | 13 | 19 | 13 | damage |

2. Growth inhibition in paddy rice

Rice plants were raised in pots in a greenhouse to the 3-leaf stage, and then treated with the compounds according to the invention. The substances were applied both by spraying and in the water.

3 weeks after treatment, the additional growth was measured in all plants and the growth inhibition calculated in % of the additional growth in the control plants. In addition, a possible phytotoxic action of the compounds was looked for.

The growth inhibition was determined as a percentage, 100% denoting cessation of growth and 0% denoting growth corresponding to that of the untreated control plants.

The results are collated in the following table.

TABLE

| Compounds according to Ex. No. | Application conc., kg/ha | Growth inhibition (%) | Phytotoxic action |
|---|---|---|---|
| 42 | 2.5 | 26 | no |
|  | 1.25 | 24 | damage |
|  | 0.62 | 20 |  |
| 43 | " | 27 | no |
|  | " | 24 | damage |
|  | " | 19 |  |
| 62 | " | 19 | no |
|  | " | 15 | damage |
|  | " | 8 |  |
| 83 | " | 21 | no |
|  | " | 16 | damage |
|  | " | 13 |  |
| 88 | " | 19 | no |
|  | " | 16 | damage |
|  | " | 12 |  |
| 178 | " | 22 | no |
|  | " | 17 | damage |
|  | " | 15 |  |
| 206 | " | 25 | no |
|  | " | 19 | damage |
|  | " | 17 |  |
| 208 | " | 32 | no |
|  | " | 27 | damage |
|  | " | 21 |  |
| 218 | " | 26 | no |
|  | " | 20 | damage |
|  | " | 17 |  |
| 219 | " | 27 | no |
|  | " | 21 | damage |
|  | " | 17 |  |
| 246 | " | 29 | no |
|  | " | 25 | damage |
|  | " | 21 |  |

3. Growth inhibition in soybeans

Soybeans, about 10 cm tall, were sprayed with the active ingredient formulations until dripping wet. Assessment was carried out after 3 weeks.

The growth inhibition was determined as a percentage, 100% denoting cessation of growth and 0% denoting growth corresponding to that of the untreated control plants.

TABLE

| Compounds according to Ex. No. | Application conc., ka/ha | Growth inhibition (%) | Phytotoxic action |
|---|---|---|---|
| 35 | 2.5 | 22 | no damage |
| 88 | 2.5 | 25 | " |
| 89 | 2.5 | 27 | " |
| 42 | 2.5 | 26 | " |
| 43 | 2.5 | 24 | " |
| 44 | 2.5 | 26 | " |

B. Safener action

EXAMPLE 1

Cereals, preferably wheat, were raised in 9 cm diameter plastic pots in a greehouse to the 3–4 leaf stage and then treated, in the post-emergence method, simultaneously with the compounds according to the invention and the herbicides tested. In this treatment, the herbicides and the compounds of the formula I were applied in the form of aqueous suspensions or emulsions at a water application rate of approximately 800 l/ha. 3–4 weeks after treatment, the plants were assessed visually for any tyupe of damage caused by the herbicides applied, the extent of lasting growth inhibition, in particular, being taken into account.

The results from Table V show that the compounds according to the invention are able to effectively reduce severe herbicide damage to the crop plants.

Even in the case of considerable overdosing of the herbicide, severe damage occurring in the crop plant is greatly reduced, and less severe symptoms of damage are completely eliminated. Mixtures of herbicides and the compounds according to the invention are therefore suitable in an excellent fashion for selective combating of weeds in cereal crops.

EXAMPLE 2

Cereals and the two weed grasses Avena fatua and Alopecurus myosuroides were sown in sandy loam in 9 cm diameter plastic pots, raised in a greenhouse under ideal growth conditions to the 3–4 leaf stage or until commencement of tillering, and treated with mixtures of the compounds according to the invention and herbicides. In this treatment, the preparations were applied in the form of aqueous suspensions or emulsions at a water application rate of approximately 300–600 l/ha.

3–4 weeks after application, the test plants were assessed visually for growth changes and damage compared to untreated controls and controls treated with the herbicides alone.

The results from Table V show that the compounds according to the invention have very good safener properties in the case of cereal plants and are thus able to effectively prevent herbicide damage without impairing the actual herbicidal action against weed grasses.

Mixtures of herbicides and the compounds according to the invention can thus be employed for selective combating of weeds.

Safener action of the compounds according to the invention. Damage to crop plants in %.

TABLE

| Example No. | herbicidal action | |
|---|---|---|
| | TA | HV |
| $H_1$ | 85 | 80 |
| $H_1$ + 16 | 40 | — |
| $H_1$ + 17 | 45 | — |
| $H_1$ + 26 | 40 | — |
| $H_1$ + 27 | 40 | — |
| $H_1$ + 30 | 50 | — |
| $H_1$ + 34 | 40 | — |
| $H_1$ + 45 | 20 | 35 |
| $H_1$ + 46 | 30 | 40 |
| $H_1$ + 47 | 30 | — |
| $H_1$ + 48 | 30 | — |
| $H_1$ + 49 | — | 50 |
| $H_1$ + 50 | 30 | — |
| $H_1$ + 51 | — | 50 |
| $H_1$ + 54 | — | 50 |
| $H_1$ + 65 | 30 | — |
| $H_1$ + 84 | 40 | 55 |
| $H_1$ + 96 | 30 | — |
| $H_1$ + 98 | 50 | — |
| $H_1$ + 99 | — | 40 |
| $H_1$ + 128 | — | 50 |
| $H_1$ + 136 | 20 | — |
| $H_1$ + 153 | 30 | 65 |
| $H_1$ + 154 | 40 | — |
| $H_1$ + 164 | 40 | — |
| $H_1$ + 178 | 50 | — |
| $H_1$ + 201 | 30 | — |
| $H_1$ + 204 | 40 | 35 |
| $H_1$ + 205 | 50 | 30 |
| $H_1$ + 209 | 50 | — |
| $H_1$ + 210 | 35 | — |
| $H_1$ + 211 | 40 | 55 |
| $H_1$ + 218 | — | 40 |
| $H_1$ + 219 | 35 | — |
| $H_1$ + 220 | 50 | — |
| $H_1$ + 237 | 40 | — |
| $H_1$ + 238 | 30 | — |
| $H_1$ + 239 | 50 | — |
| $H_1$ + 240 | 50 | — |
| $H_1$ + 246 | 40 | 30 |
| $H_1$ + 251 | 30 | — |
| $H_1$ + 252 | 30 | 40 |
| $H_1$ + 259 | 30 | — |
| $H_1$ + 260 | 40 | 50 |
| $H_1$ + 261 | 50 | 40 |
| $H_1$ + 262 | 40 | 45 |
| $H_1$ + 265 | — | 50 |
| $H_1$ + 269 | — | 50 |
| $H_1$ + 270 | 60 | 50 |
| $H_1$ + 271 | 20 | 45 |
| $H_1$ + 279 | 50 | — |
| $H_1$ + 280 | 50 | — |
| $H_1$ + 286 | 10 | 40 |
| $H_1$ + 288 | 30 | 40 |
| $H_1$ + 289 | 40 | — |
| $H_1$ + 293 | 50 | — |
| $H_1$ + 294 | 40 | — |

TABLE-continued

| Example No. | herbicidal action | |
|---|---|---|
| | TA | HV |
| $H_1$ + 295 | 50 | — |
| $H_1$ + 298 | — | 50 |
| $H_1$ + 311 | 40 | 40 |
| $H_1$ + 312 | 40 | 50 |
| $H_1$ + 314 | 40 | — |
| $H_1$ + 331 | 40 | — |
| $H_1$ + 334 | 20 | 50 |
| $H_1$ + 340 | 40 | — |
| $H_1$ + 342 | 40 | — |
| $H_1$ + 343 | 40 | — |
| $H_1$ + 344 | 40 | — |
| $H_1$ + 346 | 40 | — |
| $H_1$ + 347 | 40 | — |
| $H_1$ + 348 | 30 | — |
| $H_1$ + 349 | 20 | 50 |
| $H_1$ + 350 | 40 | 50 |
| $H_1$ + 352 | — | 50 |
| $H_1$ + 353 | 40 | — |
| $H_1$ + 371 | 40 | 35 |
| $H_1$ + 373 | 45 | 60 |
| $H_1$ + 375 | 35 | — |
| $H_1$ + 389 | 20 | 50 |
| $H_1$ + 391 | 40 | — |
| $H_1$ + 394 | 40 | — |
| $H_1$ + 395 | 40 | — |
| $H_1$ + 407 | 40 | 35 |
| $H_1$ + 408 | 35 | 35 |
| $H_1$ + 409 | 40 | 40 |
| $H_1$ + 410 | 60 | 50 |
| $H_1$ + 415 | 40 | — |
| $H_1$ + 416 | 30 | 60 |
| $H_1$ + 417 | 40 | 40 |

Explanations and abbreviations

Dosages of the mixture components:
$H_1$: 2.0 kg of a.i./ha (TA) 0.3 kg of a.i./ha (HV)
Safener: 2.5 kg of a.i./ha
$H_1$ = fenaxaprop-ethyl
TA = Triticum aestivum
HV = Hordeum vulgare

We claim:

1. A compound of formula I, and agriculturally acceptable salts and quaternization products thereof,

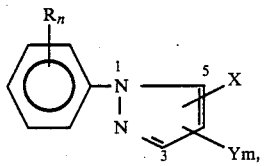

(I)

in which:

R, in each case independently of one another, is halogen, hydroxyl, cyano, nitro, $(C_1-C_4)$alkyl, halo$(C_1-C_4)$alkyl, $(C_1-C_4)$alkoxy$(C_1-C_4)$alkyl, $(C_1-C_4)$alkoxy, $(C_1-C_6)$alkoxy$(C_1-C_4)$alkoxy, halo$(C_1-C_6)$alkoxy, $(C_1-C_4)$alkylthio, halo$(C_1-C_4)$alkylthio, carboxyl, $(C_1-C_4)$alkoxycarbonyl, $(C_1-C_4)$alkylsulfinyl, halo$(C_1-C_4)$alkylsulfinyl, $(C_1-C_4)$alkylsulfonyl, halo$(C_1-C_4)$alkylsulfonyl, $(C_1-C_4)$alkylsulfonyloxy, halo$(C_1-C_4)$alkylsulfonyloxy, phenyl, halophenyl, phenoxy or halophenoxy, X is oriented in the 3- or 5-position of the pyrazole ring and is a radical of the formula

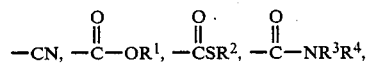

-continued

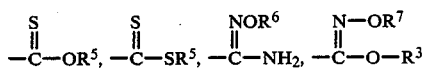

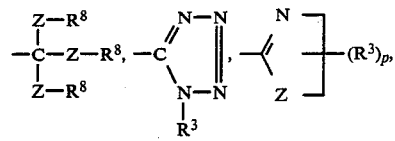

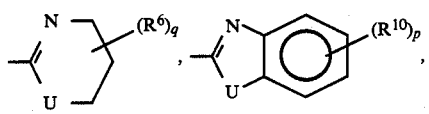

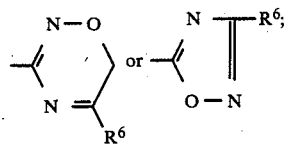

Z is O or S;
U is O, S or N-R$^6$;

R$^1$ is hydrogen, (C$_1$-C$_{12}$)alkyl, (C$_1$-C$_{12}$)alkyl which is monosubstituted or polysubstituted by halogen and/or monosubstituted or disubstituted by hydroxyl, (C$_1$-C$_6$)alkoxy, (C$_1$-C$_4$)alkoxy-(C$_1$-C$_4$)alkoxy, (C$_1$-C$_4$)alkylthio, (C$_1$-C$_4$)alkylsulfinyl, (C$_1$-C$_4$)alkylsulfonyl, mono- or di-(C$_1$-C$_4$-alkyl)amino, cyano, aminocarbonyl, (C$_1$-C$_4$)alkylcaronyl, (C$_1$-C$_4$-alkoxy)carbonyl, cyclo(C$_3$-C$_7$)alkyl, tri(C$_1$-C$_4$)alkylsilyl, benzyloxy, benzyloxyethoxy, phenyl, phenyl which is substituted by halogen or (C$_1$-C$_4$)alkyl, phenoxy or phenylthio which both are unsubstituted or substituted by halogen or (C$_1$-C$_4$)alkyl; by oxiranyl, tetrahydrofuryl, triazolyl, pyridinyl, imidazolyl, carboxyl, carboxylate with a cation which can be employed for agriculture, or the —O—N=C(CH$_3$)$_2$ radical; or is (C$_3$-C$_6$)alkenyl, halo(C$_3$-C$_6$)alkenyl, cyclo(C$_3$-C$_7$)alkyl which is unsubstituted or substituted by halogen or (C$_1$-C$_4$)alkyl; cyclo(C$_5$-C$_7$)alkenyl which is unsubstituted or substituted by halogen or (C$_1$-C$_4$)alkyl; or is (C$_3$-C$_6$)alkynyl, 1,2-epoxyprop-3-yl, phenyl or phenyl which is monosubstituted or disubstituted by halogen, nitro, cyano, (C$_1$-C$_4$)alkyl, (C$_1$-C$_4$-alkoxy)carbonyl or (C$_1$-C$_4$)alkoxy; or is (C$_1$-C$_4$-alkyl)carbonyl, phenylcarbonyl with a phenyl ring which is unsubstituted or substituted by halogen, nitro, cyano or (C$_1$-C$_4$)alkyl, or is a radical of the formula

—N=C(R$^{10}$)$_2$, —NR$^3$R$^{11}$,

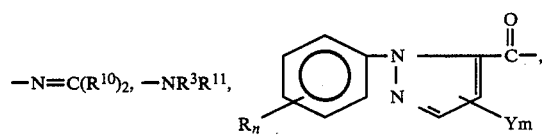

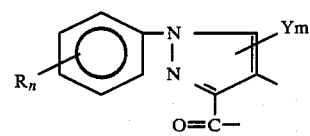

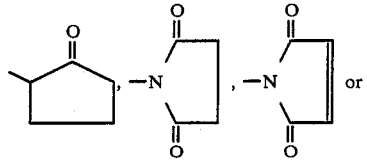

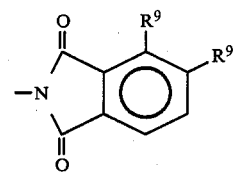

or an agriculturally acceptable cation;

R$^2$ is (C$_1$-C$_{12}$)alkyl or (C$_1$-C$_{12}$)alkyl which is monosubstituted or disubstituted by (C$_1$-C$_4$)alkoxyethoxy, cyclo(C$_3$-C$_6$)alkyl, benzyloxy, phenyl, phenoxy, (C$_1$-C$_4$)alkylthio, (C$_1$-C$_4$-alkoxy)carbonyl, carboxyl or carboxylate with an agricuturally acceptable cation;

R$^3$, in each case independently of one another, is (C$_1$-C$_6$)alkyl, phenyl or (C$_3$-C$_6$)alkenyl;

R$^4$ is hydrogen, (C$_1$-C$_{12}$)alkyl or (C$_1$-C$_{12}$)alkyl which is monosubstituted or disubstituted by (C$_1$-C$_6$)alkoxy, (C$_1$-C$_4$)alkoxyethoxy, hydroxyl, hydroxyimino, (C$_1$-C$_4$)alkoxyimino, halogen; cyclo (C$_3$-C$_6$)alkyl, benzyloxy, cyano, aminocarbonyl, carboxyl, (C$_1$-C$_4$-alkoxy)carbonyl, formyl, phenyl or phenoxy, or is phenyl or phenyl which is monosubstituted or disubstituted by halogen, nitro, cyano, (C$_1$-C$_4$)alkyl or (C$_1$-C$_4$)alkoxy; or is (C$_3$-C$_6$)alkenyl, (C$_3$-C$_6$)cycloalkyl, or a radical of the formula:

—NR$^3$R$^{12}$, —O—R$^6$, —NH—CONH$_2$,
—NH—CS—NH$_2$ or —SO$_2$R$^{13}$ or

R$^3$ and R$^4$, together with the nitrogen atom to which they are bound, are a ring selected from the group consisting of piperidine, morpholine, 2,6-dimethyl morpholine, piperazine, triazole, imidazole, pyrazole, thiazole and benzimidazole;

R$^5$ is hydrogen, (C$_1$-C$_6$)alkyl or phenyl, or in the case where X is —CS—OR$^5$, is an agriculturally acceptable cation;

R$^6$, in each case independently of one another, is hydrogen, (C$_1$-C$_4$)alkyl or benzyl;

R$^7$, in each case independently of one another, is hydrogen, (C$_1$-C$_{12}$)alkyl which is unsubstituted or substituted by phenyl which is unsubstituted or substituted by halogen, nitro, cyano, (C$_1$-C$_4$)alkyl or (C$_1$-C$_4$)alkoxy, by hydroxyl, cyano, (C$_1$-C$_4$-alkoxy)carbonyl, (C$_1$-C$_4$)alkylthio, (C$_1$-C$_4$)alkoxy, cyclo(C$_5$-C$_7$)alkyl or benzyloxy, or is (C$_3$-C$_6$)alkenyl, halo(C$_3$-C$_6$)alkenyl, (C$_3$-C$_6$)alkynyl, cyclo(C$_5$-C$_8$)alkyl, cyclo(C$_5$-C$_6$)alkenyl, (C$_1$-C$_6$-alkyl)carbonyl, halo(C$_1$-C$_6$-alkyl)carbonyl, ((C$_1$-C$_6$-alkyl)amino)carbonyl, benzoyl, halobenzoyl or methylbenzoyl;

R$^8$, in each case independently of one another, is (C$_1$-C$_6$)alkyl which is unsubstituted or substituted by phenyl, cyclo(C$_5$-C$_7$)alkyl, (C$_1$-C$_4$)alkoxy, (C$_1$-C$_4$)alkylthio or halogen, or two radicals R$^8$, together with Z and the carbon atom to which they are bound, are a 5- or 6-membered saturated heterocyclic ring which is unsubstituted or substituted by (C$_1$–C$_4$)alkyl, hydroxy(C$_1$–C$_4$)alkyl, halo(C$_1$–C$_4$)alkyl or phenyl;

R$^9$, in each case independently of one another, is hydrogen, halogen, (C$_1$–C$_4$)alkyl, nitro or cyano;

R$^{10}$, in each case independently of one another, is hydrogen, (C$_1$–C$_6$)alkyl which is unsubstituted or substituted by (C$_1$–C$_4$)alkoxy, triazolyl or imidazolyl; or is cyclo-(C$_3$–C$_6$)alkyl, (C$_3$–C$_6$)alkenyl, phenyl or benzyl, or in the radical —N=C(R$^{10}$)$_2$ both radicals R$^{10}$, together with the carbon atom to which they are bound, are a cyclo(C$_5$–C$_7$)alkyl which is unsubstituted or substituted by methyl or halogen;

R$^{11}$ is (C$_1$–C$_4$)alkyl, phenyl, (C$_1$–C$_6$-alkyl)carbonyl, benzyl, benzoyl, halobenzyl, halobenzoyl or methylbenzoyl;

R$^{12}$ is hydrogen, (C$_1$–C$_4$)alkyl, formyl (C$_1$–C$_6$-alkyl)-carbonyl, benzoyl, halobenzoyl, methylbenzoyl or trihaloacetyl;

R$^{13}$ is (C$_1$–C$_4$)alkyl, phenyl or methylphenyl;

n is an integer from 0 to 5;

p is an integer from 0 to 4; and q is an integer from 0 to 6.

2. The compound 1-(2,4-dichlorophenyl)-pyrazole-5-carboxylic acid ethyl ester.

3. The compound 1-(3-trifluormethylphenyl)-pyrazole-5-carboxylic acid cyclohexylester.

4. The compound 1-(2,4-dichlorophenyl)-pyrazole-5-carboxylic acid.

5. The compound 1-(2,4-dichlorophenyl)-pyrazole-5-carboxylic acid-thioethylester.

6. The compound 1-(2,6-diethylphenyl)-pyrazole-5-carboxylic acid.

7. The compound 1-(3-trifluormethylphenyl)-pyrazole-5-carboxylic acid.

8. A plant growth regulating composition comprising a plant growth regulating effective amount of a compound of formula I as claimed in claim 1 and an inert carrier.

9. A composition for protecting crop plants against phytotoxic side effects of a herbicide comprising a phytotoxic side effect protecting effective amount of a compound of formula I as claimed in 1 and an inert carrier.

10. A method for regulating plant growth, wherein a plant growth regulating effective amount of a compound of formula I as claimed in claim 1 is applied to a plant or to a cultivated area.

11. A method for protecting crop plants against phytotoxic side effects of a herbicide, wherein a phytotoxic side effect protecting effective amount of a compound of formula I as claimed in claim 1 is applied to the crop plants or a cultivated area before, after or at the same time the herbicide is applied.

12. The method as claimed in claim 11, wherein the herbicide is selected from the group consisting of phenoxyphenoxy-, quinolyloxy-, quinoxalyloxy-, pyridyloxy-, benzoxazolyloxy-, and benzothiazolyloxyphenoxy-carboxylates.

13. A method as claimed in claim 11, wherein the compound of formula I and said herbicide are applied in a ratio ranging between 1:10 and 10:1.

14. A method as claimed in claim 13, wherein said ratio ranges from 2:1 and 1:10.

* * * * *

UNITED STATES PATENT AND TRADEMARK OFFICE
CERTIFICATE OF CORRECTION

PATENT NO. : 4,891,057  Page 1 of 3
DATED : January 2, 1990
INVENTOR(S) : Erich Sohn, et al.

It is certified that error appears in the above-identified patent and that said Letters Patent is hereby corrected as shown below:

In col. 34, lines 42-68; col. 35, lines 1-67; col. 36, lines 1-68; and col. 37, lines 1-25, please delete claim 1 and add new claim 1, as follows:

--1. A compound of formula I, and agriculturally acceptable salts and quaternization products thereof,

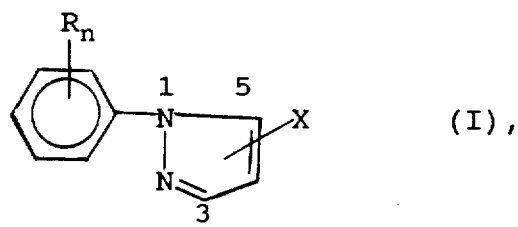

wherein:

R, in each case independently of one another, is halogen, hydroxyl, nitro, $(C_1-C_4)$alkyl, halo$(C_1-C_4)$alkyl, $(C_1-C_4)$alkoxy$(C_1-C_4)$alkyl, $(C_1-C_6)$alkoxy, $(C_1-C_6)$alkoxy$(C_1-C_4)$alkoxy, halo$(C_1-C_6)$alkoxy, $(C_1-C_4)$alkylthio, halo$(C_1-C_4)$alkylthio, $(C_1-C_4)$alkylsulfinyl, halo$(C_1-C_4)$alkylsulfinyl, $(C_1-C_4)$alkylsulfonyl, halo$(C_1-C_4)$alkylsulfonyl, phenyl, halophenyl, phenoxy or halophenoxy;

UNITED STATES PATENT AND TRADEMARK OFFICE
CERTIFICATE OF CORRECTION

PATENT NO. : 4,891,057
DATED : January 2, 1990
INVENTOR(S) : Erich Sohn, et al.

It is certified that error appears in the above-identified patent and that said Letters Patent is hereby corrected as shown below:

X     is oriented in the 3- or 5- position of the pyrazole ring and is a radical of formula $CO\text{-}OR^1$, $CO\text{-}SR^2$, $CS\text{-}OR^5$ or $CS\text{-}SR^5$;

$R^1$     is hydrogen, $(C_1\text{-}C_{12})$alkyl, $(C_1\text{-}C_{12})$alkyl which is monosubstituted or polysubstituted by halogen and/or monosubstituted or disubstituted by hydroxyl, $(C_1\text{-}C_6)$alkoxy, $(C_1\text{-}C_4)$alkylthio, $(C_1\text{-}C_4)$alkylsulfinyl, $(C_1\text{-}C_4)$alkylsulfonyl, cyclo$(C_3\text{-}C_7)$alkyl, benzyloxy, benzyloxyethoxy, phenyl, phenyl which is substituted by halogen or $(C_1\text{-}C_4)$alkyl, or is $(C_3\text{-}C_6)$alkenyl, halo$(C_3\text{-}C_6)$alkenyl, $(C_3\text{-}C_7)$cycloalkyl, cyclo$(C_5\text{-}C_7)$alkenyl, or is phenyl which is monosubstituted or disubstituted by halogen, nitro, $(C_1\text{-}C_4)$alkyl or $(C_1\text{-}C_4)$alkoxy; or an agriculturally acceptable cation;

UNITED STATES PATENT AND TRADEMARK OFFICE
CERTIFICATE OF CORRECTION

PATENT NO. : 4,891,057
DATED : January 2, 1990
INVENTOR(S) : Erich Sohn, et al.

It is certified that error appears in the above-identified patent and that said Letters Patent is hereby corrected as shown below:

$R^2$ is $(C_1-C_{12})$alkyl or $(C_1-C_{12})$alkyl which is monosubstituted or disubstituted by cyclo$(C_3-C_6)$alkyl, benzyloxy, phenoxy, $(C_1-C_4)$alkylthio or an agriculturally acceptable cation;

$R^5$ is hydrogen, $(C_1-C_6)$alkyl or phenyl, or, in the case where X is $-CS-OR^5$, is an agriculturally acceptable cation; and n is an integer from 0 to 5.--

Signed and Sealed this

Fourth Day of May, 1993

Attest:

MICHAEL K. KIRK

Attesting Officer

Acting Commissioner of Patents and Trademarks